(12) United States Patent
Fenaux et al.

(10) Patent No.: US 10,428,105 B2
(45) Date of Patent: *Oct. 1, 2019

(54) ALKYNYL NUCLEOSIDE ANALOGS AS INHIBITORS OF HUMAN RHINOVIRUS

(71) Applicant: NOVARTIS AG, Basel (CH)

(72) Inventors: Martijn Fenaux, San Mateo, CA (US);
Oliver Saunders, Clovis, CA (US);
Fumiaki Yokokawa, Dublin, CA (US);
Weidong Zhong, San Ramon, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,469

(22) Filed: May 8, 2018

(65) Prior Publication Data

US 2018/0258129 A1  Sep. 13, 2018

Related U.S. Application Data

(63) Continuation of application No. 15/465,485, filed on Mar. 21, 2017, now Pat. No. 9,988,416.

(30) Foreign Application Priority Data

Mar. 24, 2016 (SG) .......................... 10201602360R

(51) Int. Cl.
| | | |
|---|---|---|
| C07H 19/14 | (2006.01) | |
| A61K 31/7064 | (2006.01) | |
| C07D 487/04 | (2006.01) | |
| C07H 19/04 | (2006.01) | |

(52) U.S. Cl.
CPC ......... *C07H 19/14* (2013.01); *A61K 31/7064* (2013.01); *C07D 487/04* (2013.01); *C07H 19/04* (2013.01); *Y02A 50/382* (2018.01)

(58) Field of Classification Search
None
See application file for complete search history.

(56) References Cited

U.S. PATENT DOCUMENTS

| | | | | |
|---|---|---|---|---|
| 9,988,416 B2* | 6/2018 | Fenaux | .................. | C07H 19/14 |
| 2004/0229839 A1 | 11/2004 | Babu et al. | | |
| 2015/0366888 A1* | 12/2015 | Blatt | .................... | A61K 31/708 |
| | | | | 514/47 |

FOREIGN PATENT DOCUMENTS

| | | |
|---|---|---|
| WO | WO 1998/016184 | 4/1998 |
| WO | WO 2002/057425 | 7/2002 |
| WO | WO 2010/075554 | 7/2010 |
| WO | WO 2010/108140 | 9/2010 |
| WO | WO 2012/012465 | 1/2012 |
| WO | WO 2014/100505 | 1/2014 |
| WO | WO 2014/209979 | 12/2014 |
| WO | WO 2015/054465 | 4/2015 |
| WO | WO 2015/200219 | 12/2015 |

OTHER PUBLICATIONS

Shang et al., Antiviral research, 112: 47-58, 2014.*
Fu et al., "Development of a FACS-based assay for evaluating antiviral potency of compound in dengue infected peripheral blood mononuclear cells" Journal of Virological Methods 196:18-24, 2014.
Shang et al., "An adenosine nucleoside analogue NITD008 inhibits EV71 proliferation" Antiviral Research 112:47-58, 2014.
Shi et al., "Synthesis and Antiviral Activity of 2'-Deoxy-2'-Fluoro-2'-C-Methyl-7-Deazapurine Nucleosides, Their Phosphoramidate Prodrugs and 5'-Triphosphates" Bioorg Med Chem Lett 21(23):7094-7098, 2011.

* cited by examiner

*Primary Examiner* — Traviss C McIntosh, III
(74) *Attorney, Agent, or Firm* — Mark H. Hopkins

(57) ABSTRACT

The present invention provides a compound of Formula (I) or a salt thereof;

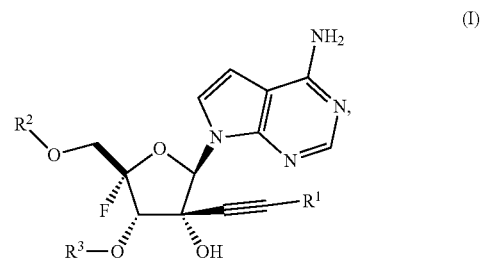

and therapeutic uses of these compounds. The invention further provides pharmaceutical compositions comprising these compounds, and compositions comprising these compounds with a therapeutic co-agent, and methods of using the compounds and compositions for treatment of viral infections, especially HRV.

16 Claims, No Drawings
Specification includes a Sequence Listing.

ALKYNYL NUCLEOSIDE ANALOGS AS INHIBITORS OF HUMAN RHINOVIRUS

CROSS-REFERENCE TO RELATED APPLICATIONS

This application is a continuation of U.S. Ser. No. 15/465,485, filed Mar. 21, 2017, which claims the benefit of priority to Singapore patent application No. 10201602360R, filed Mar. 24, 2016, the contents of which are incorporated herein by reference.

FIELD OF THE INVENTION

The present invention relates to compounds that inhibit human rhinovirus (HRV) replication and are useful for treating subjects infected with HRV.

BACKGROUND

Human rhinoviruses (HRV) are RNA viruses in the Enterovirus genus of the Picomavirus family, and are divided into three groups, HRV-A, HRV-B and HRV-C, based on sequence analysis. These viruses cause a variety of upper and lower respiratory tract infections (RTIs). Typically the upper RTIs are not especially serious in healthy subjects, manifesting as the common cold, but they can lead to more serious conditions such as acute otitis media and rhinosinusitis. Lower RTIs caused by HRV can be more severe, particularly in susceptible populations; for example, they can cause serious exacerbations in subjects with COPD, asthma, or cystic fibrosis, and severe, sometimes fatal pneumonia in infants, the elderly, and immunocompromised subjects.

In spite of the need for antiviral therapeutic agents to treat diseases caused by HRV, there are no approved HRV antivirals in the U.S. Mello, et al., *Antimicrobial Agents and Chemotherapy*, 58(3), 1546-55 (2014). Various antiviral agents with different modes of action have been tested against HRV, e.g., capsid-binding inhibitors (pleconaril, pirodavir), 3C protease inhibitors (rupintrivir), and nucleoside analogs (MK-0608, an inhibitor of 3D polymerase), and PI4K-IIIβ inhibitors (PIK93), but none have passed clinical trials. Id.

Nucleoside compounds having antiviral activity are well known in the art; for example, AZT is used to treat HIV infections. It acts as an inhibitor of reverse transcriptase, inhibiting an enzyme HIV requires in order to synthesize DNA, thus inhibiting HIV replication. Various nucleoside analogs have been shown to have activity on hepatitis C virus (HCV)—see, e.g., Smith, et al., *J. Med. Chem.* 52(1), 219-23 (2009); WO2012/040124; WO2011/100131; and US2012/0070415. None, however, have been developed to treat human rhinovirus infections.

One of the complications of treating HRV is the large number of different strains: over 160 strains of HRV are known, and if a therapeutic for treating HRV is not effective on most of the common strains, it would be necessary to determine which strain a patient has before treatment. That is not practical in most situations at present, so an antiviral with broad-spectrum activity on various HRV strains would be especially valuable.

Thus there remains a need for antiviral agents useful to treat HRV infections, particularly in populations susceptible to the more serious effects of HRV infection. The present invention provides such antiviral compounds and pharmaceutical compositions containing these compounds, as well as methods of using the compounds and compositions for treatment of subjects having or at risk of HRV infections.

SUMMARY OF THE INVENTION

The invention provides compounds that inhibit human rhinovirus (HRV) replication. The compounds reduce or prevent spreading of HRV to uninfected cells, and are thus useful to reduce the duration or severity of HRV infections. By reducing the extent, severity or duration of HRV infections, these compounds protect against exacerbation of other conditions in susceptible populations such as infants and elderly or immunocompromised subjects, and subjects having asthma, COPD or cystic fibrosis. The compounds are also useful to inhibit the replication of HRV in an isolated cell or a cell culture.

In one aspect, the invention provides a compound of formula (I):

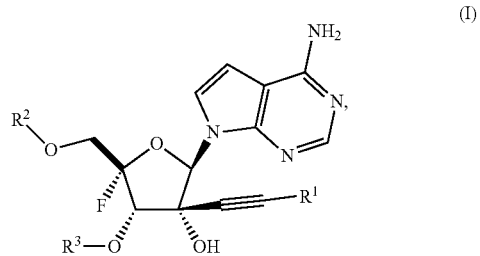

as further described herein, along with pharmaceutical combinations and compositions comprising these compounds and methods to use the compounds, combinations and compositions for treating certain viral infections.

The compounds of Formula (I) are inhibitors of HRV replication, as demonstrated by data provided herein, and are useful to treat conditions caused by HRV. Moreover, as demonstrated by data herein, compounds of Formula (I) have activity against a broad range of serotypes of HRV and show little activity in commonly-used toxicology model tests.

In another aspect, the invention provides pharmaceutical compositions comprising a compound of Formula (I) admixed with at least one pharmaceutically acceptable carrier or excipient, optionally admixed with two or more pharmaceutically acceptable carriers or excipients.

In another aspect, the invention provides a method to treat a condition caused by a human rhinovirus, which comprises administering to a subject in need of such treatment an effective amount of a compound of Formula (I) or any subgenus or species thereof as described herein, or a pharmaceutical composition comprising such compound. The subject can be a mammal, and is preferably a human. Typically the subject has been diagnosed as having an HRV infection. Conditions treatable by the compounds and methods described herein include the common cold and complications or exacerbations triggered by rhinoviral infections.

The invention includes compounds of Formula (I) and the subgenera of Formula (I) described herein, and all isotopically enriched versions thereof (including deuterium substitutions) as well as pharmaceutically acceptable salts of these compounds. Compounds of the present invention also comprise polymorphs of compounds of formula (I) (or subformulae thereof) and salts and solvates of compounds of Formula (I).

DETAILED DESCRIPTION

The following definitions apply unless otherwise indicated expressly or by context.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having 1 to 6 carbon atoms, or 1 to 4 carbon atoms. Typically, alkyl groups have 1-6 carbon atoms if not otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, and the like. A substituted alkyl is an alkyl group containing one or more substituents in place of hydrogen, such as one, two or three substituents, up to the number of hydrogens present on the unsubstituted alkyl group. Suitable substituents for alkyl groups, if not otherwise specified, are selected from halogen, CN, oxo (=O), hydroxy, $C_{1-4}$ alkoxy, substituted or unsubstituted $C_{3-6}$ cycloalkyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, COO($C_{1-4}$ alkyl), —O(C=O)—$C_{1-4}$ alkyl, —NHC(=O)$C_{1-4}$ alkyl and —NHC(=O)O$C_{1-4}$ alkyl groups.

As used herein, the term "alkoxy" refers to alkyl-O—, wherein alkyl is as defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable substituents are selected from the substituents listed above for alkyl groups, except that hydroxyl and amino are not normally present on the carbon that is directly attached to the oxygen of the substituted 'alkyl-O' group.

The following enumerated embodiments are representative of some aspects of the invention. It will be recognized that features specified in each embodiment may be combined with other specified features to provide further embodiments of the present invention.

1. A compound of formula (I):

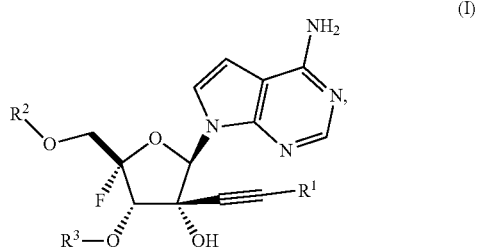

wherein:

$R^1$ is H, Me, Et, iPr, or cyclopropyl;

$R^2$ is H, phosphate, diphosphate, triphosphate, —P(=X)(OR$^4$)$_2$, —P(=X)(OR$^4$)(NR$^5$R$^6$), or —P(=X)(NR$^5$R$^6$)$_2$, and $R^3$ is H or —C(O)R;

or $R^3$ and $R^2$ taken together form —P(=X)(OR$^4$)— or —P(=X)(NR$^5$R$^6$)—;

X at each occurrence is independently O or S;

$R^4$ is selected from H, phenyl optionally substituted with one or two groups selected from List A, and $C_1$-$C_4$ alkyl optionally substituted with one or two groups selected from halo, —OR, —OC(O)R, —OC(O)—OR, —NR$_2$, —C(O)R, COOR and —C(O)NR$_2$;

each $R^5$ is independently H, —C(O)R, COOR, or $C_1$-$C_4$ alkyl optionally substituted with OH, amino, or COOR;

each $R^6$ is independently selected from H, phenyl optionally substituted with one or two groups selected from List A, and $C_1$-$C_4$ alkyl optionally substituted with one or two groups selected from List B;

each R is independently H or a $C_1$-$C_4$ alkyl group optionally substituted with one to three groups selected from halo, hydroxy, CN, amino, $C_1$-$C_3$ alkoxy, —C(O)R$^7$, —OC(O)R$^7$, —C(O)—OR$^7$, or —OC(O)—OR$^7$;

$R^7$ is selected from H, $C_1$-$C_4$ alkyl optionally substituted with one to three groups selected from halo, hydroxy, CN, amino, and $C_1$-$C_3$ alkoxy, or phenyl optionally substituted with one or two groups selected from List A;

List A is halo, hydroxy, —NO$_2$, CN, —OR$^8$, —OC(O)R$^8$, —OC(O)—OR$^8$, —N(R$^8$)$_2$, —C(O)R$^8$, COOR, —C(O)N(R$^8$)$_2$, and $C_1$-$C_3$ alkyl optionally substituted with one to three groups selected from halo, hydroxy, CN, amino, and $C_1$-$C_3$ alkoxy;

List B is halo, hydroxy, oxo, CN, —OR$^8$, —OC(O)R$^8$, —OC(O)—OR$^8$, —N(R$^8$)$_2$, —C(O)R$^8$, COOR$^8$ and —C(O)N(R$^8$)$_2$; and $R^8$ is independently at each occurrence selected from H and $C_1$-$C_4$ alkyl optionally substituted with one to three groups selected from halo, hydroxy, CN, amino, and $C_1$-$C_3$ alkoxy, and two $R^8$ attached to the same nitrogen atom can optionally cyclize to form a 3-7 membered heterocycle, which optionally contains an additional N, O or S as a ring member, and can be substituted by one or two groups selected from oxo, halo, —OH, amino, $C_1$-$C_3$ alkyl, $C_1$-$C_3$ alkoxy, and $C_1$-$C_3$ haloalkyl;

or a pharmaceutically acceptable salt thereof.

2. The compound of embodiment 1, wherein $R^1$ is methyl.

3. The compound of embodiment 1 or embodiment 2, wherein $R^2$ is H.

4. The compound of embodiment 1 or 2, wherein $R^2$ is phosphate, diphosphate or triphosphate, or a pharmaceutically acceptable salt thereof.

5. The compound of embodiment 1 or embodiment 2, wherein $R^2$ is —P(=X)(OR$^4$)$_2$, or a pharmaceutically acceptable salt thereof.

6. The compound of embodiment 5, wherein each $R^4$ is selected from —CH$_2$—O—C(O)—R or and —CH$_2$—O—C(O)—OR, wherein each R is independently $C_1$-$C_4$ alkyl, or a pharmaceutically acceptable salt thereof.

7. The compound of embodiment 1 or 2, wherein $R^3$ and $R^2$ taken together form —P(=O)(OR$^4$)— or —P(=O)—(NR$^5$R$^6$)—, or a pharmaceutically acceptable salt thereof.

8. The compound of any of the preceding embodiments, wherein $R^3$ is H.

9. The compound of embodiment 1, which is:

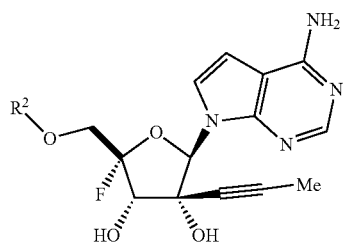

wherein $R^2$ is H, phosphate, diphosphate, or triphosphate; or a pharmaceutically acceptable salt thereof.

10. The compound of embodiment 1 or 2, which is of the formula:

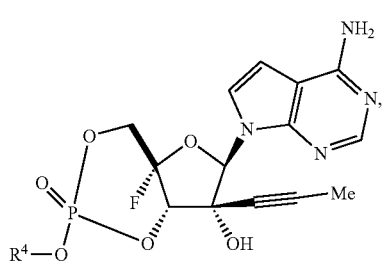

or a pharmaceutically acceptable salt thereof.

11. The compound of embodiment 1, which is of the formula:

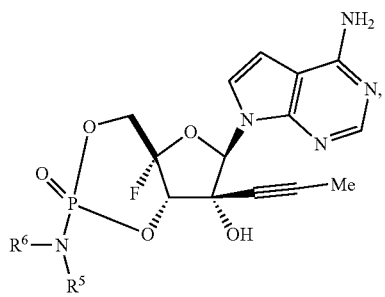

or a pharmaceutically acceptable salt thereof.

12. The compound of claim 1, which is selected from:

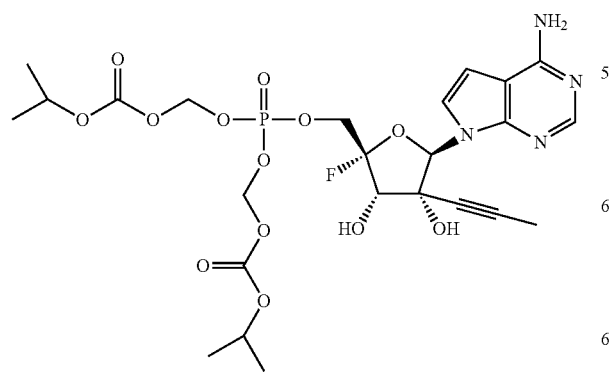

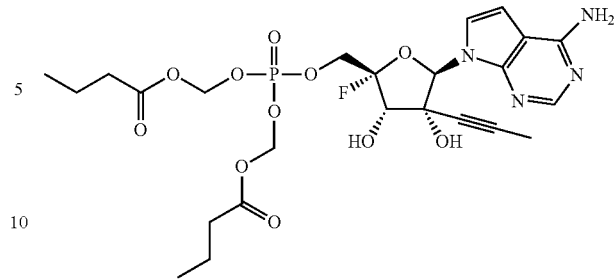

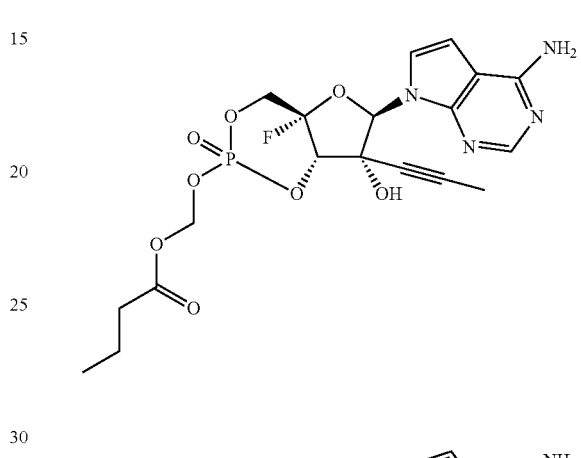

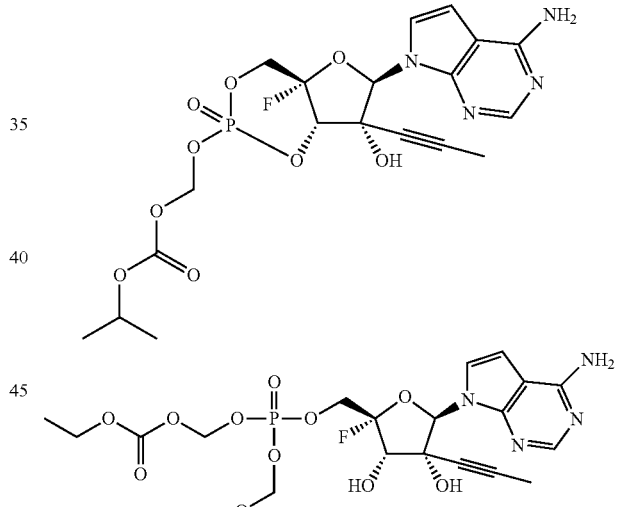

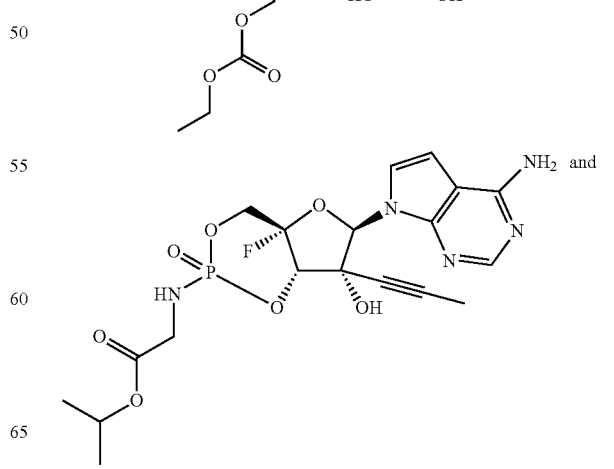

-continued

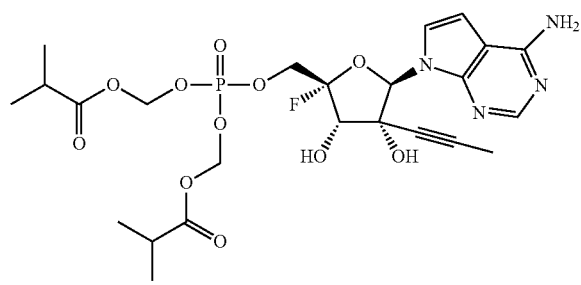

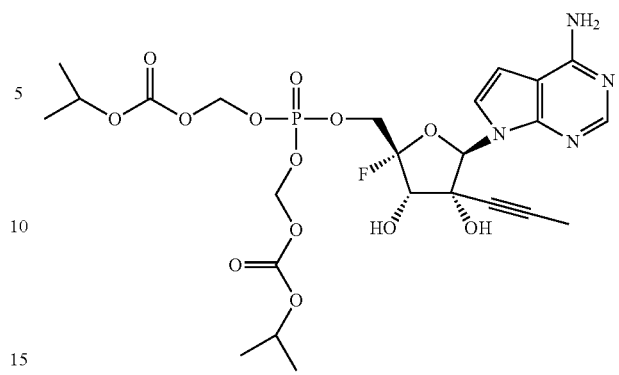

or a pharmaceutically acceptable salt thereof.

13. A pharmaceutical composition comprising a compound of any of the preceding embodiments or a pharmaceutically acceptable salt thereof and one or more pharmaceutically acceptable carriers.

14. A combination comprising a therapeutically effective amount of a compound according to any one of embodiments 1 to 12 or a pharmaceutically acceptable salt thereof and one or more therapeutically active co-agents.

15. A method of treating an HRV infection, comprising administering to a subject in need thereof a therapeutically effective amount of a compound of any of embodiments 1-12 or a pharmaceutically acceptable salt thereof.

16. A compound according to any one of embodiments 1 to 12 or a pharmaceutically acceptable salt thereof, for use as a medicament.

17. A compound according to any one of embodiments 1 to 12 or a pharmaceutically acceptable salt thereof, for use in the treatment of a human rhinovirus infection.

18. Use of a compound according to any one of embodiments 1 to 12 or a pharmaceutically acceptable salt thereof in the manufacture of a medicament for the treatment of a human rhinovirus infection.

Compounds of Formula (I) include certain derivatives and prodrugs of the nucleoside of this general formula:

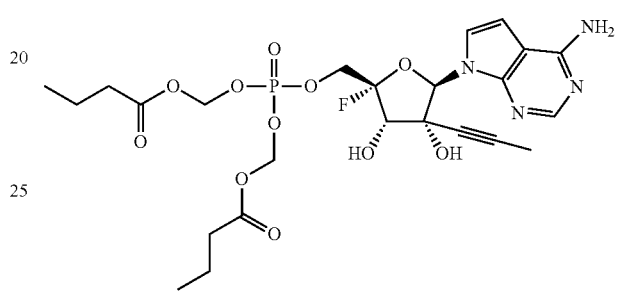

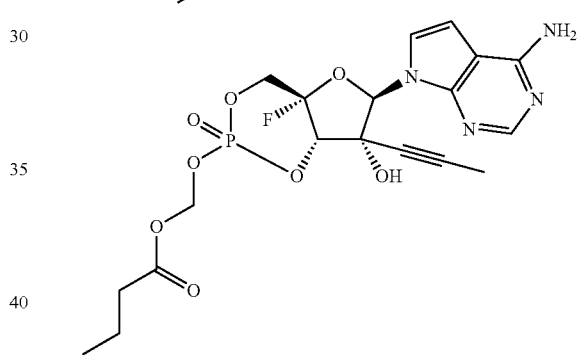

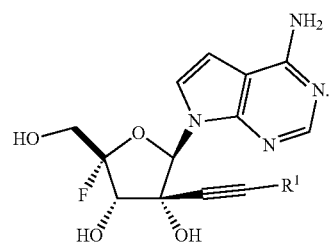

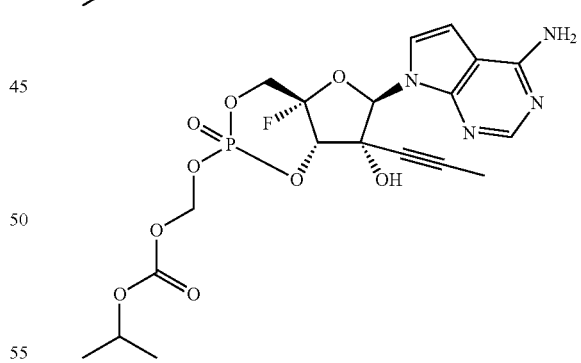

The prodrugs are compounds that are readily converted in vivo into an active form of the nucleoside, e.g., the free nucleoside, or its phosphate or triphosphate ester. Suitable prodrug moieties and methods of incorporating them into a nucleoside analog are known in the art, and illustrative examples are provided herein. Exemplary pro-drugs compounds of Formula (I) include the following:

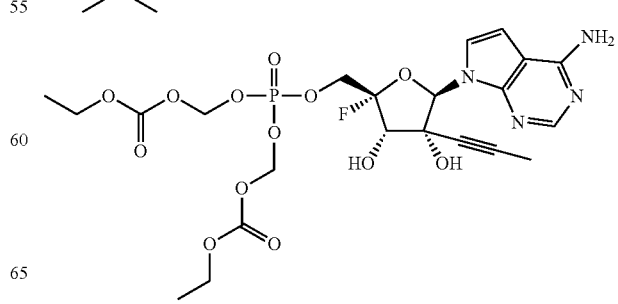

-continued

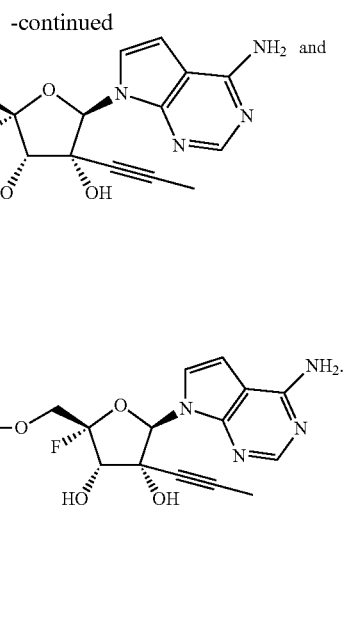

Without being bound by theory, it is believed the compounds of Formula (I) provide their biological activity in vivo after conversion to a C-5 triphosphate, e.g.:

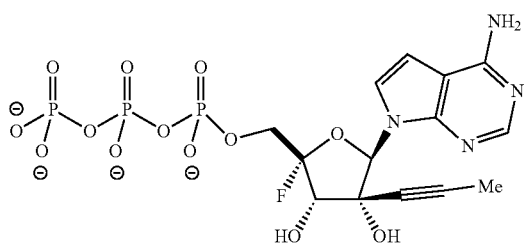 [SMILES: CC#C[C@]1(O)[C@H](n2ccc3c(N)ncnc32)O[C@](F)(COP(=O)([O-])OP(=O)([O-])OP(=O)([O-])[O-])[C@H]1O]

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. The invention includes enantiomers, diastereomers and racemates of the compound. "Enantiomers" are a pair of stereoisomers that are non-superimposable mirror images of each other. A 1:1 mixture of a pair of enantiomers is a "racemic" mixture. "Diastereoisomers" are stereoisomers that have at least two asymmetric atoms, but which are not mirror-images of each other. The absolute stereochemistry of compounds of the invention is specified according to the Cahn-lngold-Prelog 'R-S' system in compound names; where structures are drawn, a single isomer is typically shown, using accepted drawing conventions to show absolute stereochemistry. Unless otherwise specified, a compound drawn as a specific enantiomer represents that enantiomer, and describes a compound that is at least 90% and preferably at least 95% enantiomerically pure. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a di-substituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is intended to represent unlabeled forms (i.e., compounds wherein all atoms are present at natural isotopic abundances, and not isotopically enriched), as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those in which radioactive isotopes, such as $^3$H and $^{14}$C, or those in which non-radioactive isotopes, such as $^2$H and $^{13}$C, are present at levels significantly above the natural abundance for these isotopes. These isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the desired biological or medical response in a subject, for example, reduction or inhibition of an enzyme or a protein activity, or that will ameliorate symptoms, alleviate conditions, slow or delay disease progression, or prevent a disease, etc. In one non-limiting embodiment, the term "a therapeutically effective amount" refers to the amount of a compound of the present invention that, when administered to a subject, is effective to at least partially alleviate, inhibit, prevent and/or ameliorate a condition, disorder or disease caused by HRV, or reduce or inhibit the activity of HRV proteins, or reduce or inhibit the replication of HRV.

In another non-limiting embodiment, the term "a therapeutically effective amount" refers to an amount of a compound of the present invention that, when administered to a cell, or a tissue, or a non-cellular biological material, or a medium, is effective to at least partially reduce or inhibit the replication of HRV.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched quantity, for example the (R)-, (S)- or (R,S)-configuration, unless the name or depiction specifies one configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer; thus a compound depicted, named or described as a single enantiomer consists predominantly of that enantiomer, accompanied by 10% or less and preferably 5% or less of the opposite enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 10%, typically less than 5%, and preferably less than 2%, of other isomers relative to the amount of the preferred isomer, by weight.

Mixtures of isomers can be separated on the basis of the physicochemical differences of the constituents, into the pure or substantially pure geometric or optical isomers, diastereomers, racemates, for example, by chromatography and/or fractional crystallization. Methods for such separation are well established in the art.

Where needed, racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. In some embodiments, the pharmaceutical composition comprises two pharmaceutically acceptable carriers, or more than two pharmaceutically acceptable carriers. The pharmaceutical composition can be formulated for particular routes of administration such as oral administration, parenteral administration, and rectal administration, and the like. In preferred embodiments, the pharmaceutical composition is designed for either oral delivery or inhalation. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

In certain embodiments, the pharmaceutical compositions of the invention are formulated for oral delivery. Typically, these pharmaceutical compositions are tablets or gelatin capsules comprising the active ingredient together with one or more excipients selected from these:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may optionally be film coated or enteric coated by methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In other embodiments, the pharmaceutical compositions of the compounds of Formula (I) are suitable for parenteral administration, such as by injection or infusion. Certain of these compositions include aqueous isotonic solutions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ocular applications. Such may contain solubilizers, stabilizers, tonicity enhancing agents, buffers and preservatives.

As used herein a topical application may also pertain to an inhalation or to an intranasal application. The compounds of the invention are effective to treat infections that frequently are localized in the upper respiratory tract, and therefore lend themselves well to delivery via inhalation or intranasal methods. The compounds and compositions of the invention may be conveniently delivered in the form of a dry powder from a dry powder inhaler or an aerosol spray presentation from a pressurized container, pump, spray, atomizer or nebulizer, with or without the use of a suitable propellant. They may be administered either alone, as a mixture, for example a dry blend with lactose, or a mixed component particle, for example with phospholipids. Methods for preparing and delivering compounds via inhalation re known in the art.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. they inhibit replication of HRV as shown by test data provided in the next sections, and are therefore indicated for therapy as described herein, and also for use as research chemicals, e.g. as tool compounds for analyzing the effects of rhinoviral infections. The compounds and compositions containing them may therefore be used to treat infections caused by HRV in patients in need of such treatment, including the common cold, and for prevention or suppression of complications of asthma, COPD, cystic fibrosis, and other conditions that are often exacerbated by rhinovirus infections.

The compounds and compositions and methods described herein are especially useful in patients who may experience serious complications from HRV infections. For example, a subject afflicted with asthma, COPD, or cystic fibrosis may be at risk for serious complications when infected by HRV. Rhinoviral infections are a common trigger of asthma exacerbations, and are often implicated in other respiratory diseases such as otitis media, sinusitis, pneumonia, and exacerbations of COPD and cystic fibrosis. Q. J. Med. 94:1-3 (2001). Thus while a cold may be an inconvenience for an otherwise healthy person and may not necessarily warrant pharmaceutical intervention, a subject having a condition such as asthma, COPD, or cystic fibrosis, or an immunocompromised or immunosuppressed subject, or a subject who is especially susceptible to secondary respiratory tract infections like pneumonia, is particularly suitable for treatment with the compounds and methods described herein; such treatment reduces the likelihood of and/or the severity of an exacerbation event.

Thus, as a further embodiment, the present invention provides the use of a compound of formula (I) or any of the embodiments within the scope of Formula (I) as described herein, in therapy. In a particular embodiment, the therapy is for a disease caused by a strain of HRV. In another embodiment, the compounds of the invention are useful in therapy to treat rhinoviral infections in subjects with conditions such as asthma, COPD, or cystic fibrosis, immunocompromised or immunosuppressed subjects, and subjects who are especially susceptible to serious secondary respiratory tract infections like pneumonia, or to reduce the risk of occurrence of HRV infection in these sensitive subjects.

In another embodiment, the invention provides a method of treating a disease which is treated by inhibition of HRV replication, comprising administration of a therapeutically effective amount of a compound of formula (I) or any of the embodiments within the scope of Formula (I) as described herein. In a further embodiment, the disease is selected from the aforementioned conditions. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician. In some embodiments, the compound or pharmaceutical composition of the invention is administered orally. In other embodiments, the compound or pharmaceutical composition of the invention is administered nasally or by inhalation.

A further embodiment of the present invention provides the use of a compound of formula (I) or any of the embodiments of such compounds described herein for the manufacture of a medicament. In a particular embodiment, the medicament is for treatment of a disease or condition caused by or exacerbated by HRV. In particular embodiments, the disease is a rhinoviral infection, particularly in a subject with a condition such as asthma, COPD, or cystic fibrosis, an immunocompromised or immunosuppressed subject, or a subject who is especially susceptible to secondary respiratory tract infections like pneumonia.

The pharmaceutical composition or combination of the present invention can be in unit dosage of about 1-5000 mg of active ingredient(s) for a subject of about 50-70 kg, or about 1-2000 mg or about 1-500 mg or about 1-250 mg or about 0.5-100 mg, or about 1-50 mg of active ingredients. Lower doses such as 1-250 mg or 1-50 mg may be used for topical administration methods, including intranasal or inhalation administrations, and for injection or infusion, while higher doses, e.g., 25-2500 mg, or 50-5000 mg, may be used for oral administration. The therapeutically effective dosage of a compound, the pharmaceutical composition, or the combinations thereof, is also dependent on the species of the subject, the body weight, age and individual condition, and the disorder or disease being treated or the severity thereof. A physician, clinician or veterinarian of ordinary skill can readily determine the effective amount of each of the active ingredients necessary to treat or inhibit the progression of the disorder or disease.

The above-cited dosage properties are demonstrable via in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations.

The compound of the present invention may be administered either simultaneously with, or before or after, one or more therapeutic co-agent(s). The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition caused or exacerbated by HRV. Products provided as a combined preparation include a composition comprising the compound of formula (I) and the other therapeutic co-agent(s) together in the same pharmaceutical composition, or the compound of formula (I) and the other therapeutic co-agent(s) in separate form, e.g. in the form of a kit.

In one embodiment, the invention provides a pharmaceutical composition comprising a compound of formula (I) and another therapeutic co-agent(s). Optionally, the pharmaceutical composition may comprise a pharmaceutically acceptable carrier, as described above.

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). PD-1 is expressed on activated B cells, T cells, and monocytes. PD-1 is an immune-inhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J Immunol.* 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antibacterial compounds, these immunomodulators can enhance the antimicrobial response, and thus enhance efficacy relative to treatment with the antibacterial compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antibacterial compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-L1 inhibitor such as anti-PD-L1 antibody.

In some embodiments, the immunomodulator is an anti-PD-L1 binding antagonist chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 is an anti-PD-L1 described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents useful as immunomodulators for methods of the invention include YW243.55.S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antibacterial compounds of the invention in combination with an immunomodulator include these:

i. A method to treat a bacterial infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016.

xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg, e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition caused by or exacerbated by HRV, wherein the medicament is prepared for administration with another therapeutic agent. The invention also provides the use of another therapeutic co-agent for treating a disease or condition, wherein the medicament is administered with a compound of formula (I). Suitable co-agents for use in combination with compounds of the invention include 3A inhibitors, 3C protease inhibitors, and capsid binders affecting HRV, including enviroxime, pleconaril, and rupintrivir.

The invention also provides a compound of formula (I) for use in a method of treating a disease or condition caused or exacerbated by HRV, wherein the compound of formula (I) is prepared for administration with another therapeutic agent. The invention also provides another therapeutic co-agent for use in a method of treating a disease or condition caused or exacerbated by HRV, wherein the other therapeutic co-agent is prepared for administration with a compound of formula (I). The invention also provides a compound of formula (I) for use in a method of treating a disease or condition caused or exacerbated by HRV, wherein the compound of formula (I) is administered with another therapeutic co-agent. The invention also provides another therapeutic co-agent for use in a method of treating a disease or condition caused or exacerbated by HRV, wherein the other therapeutic co-agent is administered with a compound of formula (I).

The invention also provides the use of a compound of formula (I) for treating a disease or condition caused by or exacerbated by HRV, wherein the patient has previously (e.g. within 24 hours) been treated with another therapeutic agent. The invention also provides the use of another therapeutic agent for treating a disease or condition caused by or exacerbated by HRV, wherein the patient has previously (e.g. within 24 hours) been treated with a compound of formula (I).

In one embodiment, the other therapeutic agent is selected from 3A inhibitors, 3C protease inhibitors, and capsid binders affecting HRV, including enviroxime, pleconaril, and rupintrivir.

EXAMPLES

The following examples are intended to illustrate the invention and are not to be construed as limiting the scope of the invention. Temperatures are given in degrees Celsius. If not mentioned otherwise, all evaporations are performed under reduced pressure, typically between about 15 mm Hg and 100 mm Hg (20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis*, Thieme, Volume 21). Further, the compounds of the present invention can be produced by organic synthesis methods known to one of ordinary skill in the art in view of the following examples.

Example 1

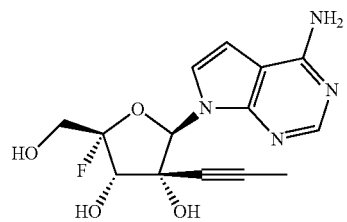 [SMILES: CC#C[C@]1(O)[C@H](n2ccc3c(N)ncnc32)O[C@](F)(CO)[C@H]1O]

Example 1 was made by the following sequence of reactions.

Synthesis of (3R,4R,5R)-4-((2,4-dichlorobenzyl)oxy)-5-(((2,4-dichlorobenzyl)oxy)methyl)-2-methoxy-3-(prop-1-yn-1-yl)tetrahydrofuran-3-ol

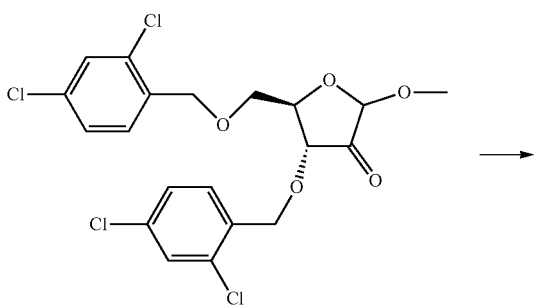

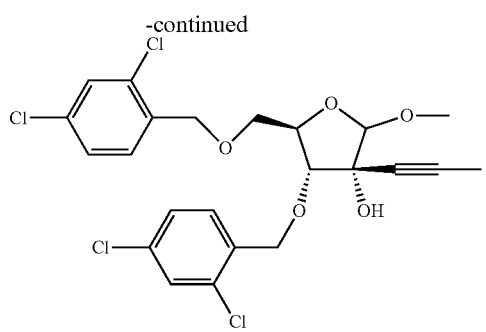

0.5 M prop-1-ynylmagnesium bromide (144 mL, 0.072 mol) was added to a solution of (4R,5R)-4-(2,4-dichlorobenzyloxy)-5-((2,4-dichlorobenzyloxy)methyl)-2-methoxydihydrofuran-3(2H)-one (CAS 636581-82-3, 11.5 g, 0.023 mol) in THF (150 mL) at −78° C. over a period of 30 min. The reaction mixture was slowly allowed to attain room temperature and stirred for 4 h. After completion of the reaction, it was cooled to 0° C. and quenched with sat. aq. NH₄Cl. Reaction mixture was extracted with EtOAc and the organic layer was washed with water followed by brine solution. The organic layer was dried over Na₂SO₄, filtered and concentrated in vacuo. The residue was purified by silica gel column chromatography to give (3R,4R,5R)-4-(2,4-dichlorobenzyloxy)-5-((2,4-dichlorobenzyloxy)methyl)-2-methoxy-3-(prop-1-ynyl)tetrahydrofuran-3-ol (6.12 g, 0.012 mmol, yield 48%). ¹HNMR (CDCl₃, 400 MHz) δ 1.83 (s, 3H), 3.40 (s, 1H), 3.49 (s, 3H), 3.70 (dd, J=4.8, 2.0 Hz, 2H), 3.86 (d, J=4.4 Hz, 1H), 4.21 (q, J=4.8 Hz, 1H), 4.61 (ABq, J=13.2 Hz, 2H), 4.70 (d, J=13.2 Hz, 1H), 4.88 (s, 1H), 4.89 (d, J=12.0 Hz, 1H), 7.18-7.24 (m, 2H), 7.35 (dd, J=6.8, 2.0 Hz, 2H), 7.40 (dd, J=8.0, 2.8 Hz, 2H).

Synthesis of (3R,4R,5R)-4-((2,4-dichlorobenzyl)oxy)-5-(((2,4-dichlorobenzyl)oxy)methyl)-3-(prop-1-yn-1-yl)tetrahydrofuran-2,3-diol

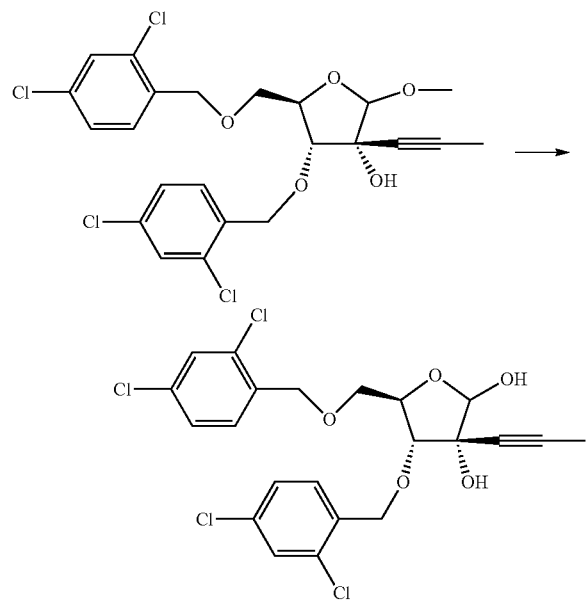

Trifluoroacetic acid (164.25 mL) in water (11.6 mL) was added to (3R,4R,5R)-4-(2,4-dichlorobenzyloxy)-5-((2,4-dichlorobenzyloxy)methyl)-2-methoxy-3-(prop-1-ynyl)tetrahydrofuran-3-ol (50.0 g, 0.096 mol) at 0° C. The reaction mixture was heated to 55° C. for 4 h. The mixture was concentrated under reduced pressure followed by co-distillation with toluene twice. The crude obtained was purified by silica gel column chromatography to give (3R,4R,5R)-4-(2,4-dichlorobenzyloxy)-5-((2,4-dichlorobenzyloxy)methyl)-3-(prop-1-ynyl)tetrahydrofuran-2,3-diol (40.10 g, 0.079 mol, yield 82%). ¹H NMR (CDCl₃, 400 MHz) δ 1.86, 1.92 (s×2, 3H), 3.44, 3.90 (brs×2, 1H), 3.58-3.65 (m, 1H), 3.69-3.74 (m, 1H), 4.10-4.15 (m, 2H), 4.59 (ABq, J=13.2 Hz, 2H), 4.75 (d, J=12.4 Hz, 1H), 4.95 (d, J=12.8 Hz, 1H), 5.10, 5.31 (s×2, 1H), 7.22-7.25 (m, 2H), 7.33-7.40 (m, 4H).

Synthesis of (1R,3R,4R,5R)-4-((2,4-dichlorobenzyl)oxy)-3-(((2,4-dichlorobenzyl)oxy)methyl)-5-(prop-1-yn-1-yl)-2,6-dioxabicyclo[3.1.0]hexane

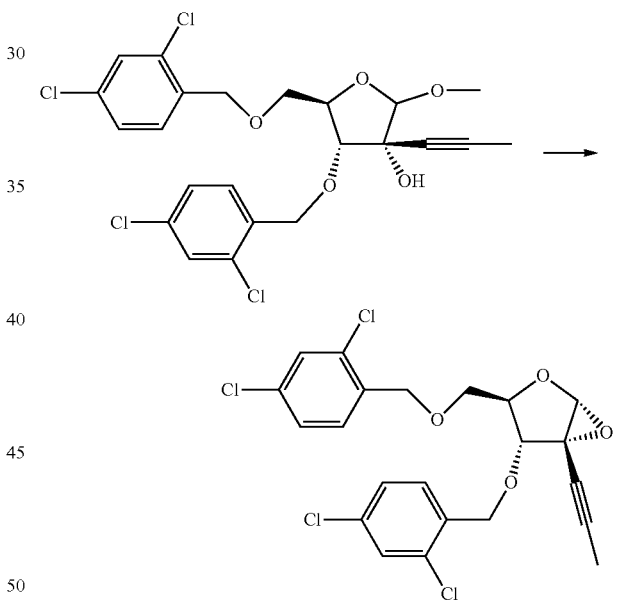

To a solution of (3R,4R,5R)-4-(2,4-dichlorobenzyloxy)-5-((2,4-dichlorobenzyloxy)methyl)-3-(prop-1-ynyl)tetrahydrofuran-2,3-diol (1.0 g, 1.9 mmol) in CH₂Cl₂ (50 mL), Et₃N (0.9 mL, 0.0059 mol) was added followed by DMAP (cat) at room temperature. The reaction mixture was cooled to 0° C. and then p-TsCl (0.615 g, 2.9 mol) was added in one lot. The resultant reaction mixture was stirred at room temperature for 3 h. After completion of the reaction, the reaction mixture was diluted with CH₂Cl₂ and organic layer was washed with water and brine. The organic layer was dried over Na₂SO₄, filtered, and concentrated in vacuo to give (1R,3R,4R,5R)-4-(2,4-dichlorobenzyloxy)-3-((2,4-dichlorobenzyloxy)methyl)-5-(prop-1-ynyl)-2,6-dioxabicyclo[3.1.0]hexane (1.2 g). This crude compound was directly used for next step.

Synthesis of (2R,3R,4R,5R)-2-(4-chloro-7H-pyrrolo[2,3-d]pyrimidin-7-yl)-4-((2,4-dichloro-benzyl)oxy)-5-(((2,4-dichlorobenzyl)oxy)methyl)-3-(prop-1-yn-1-yl)tetrahydrofuran-3-ol

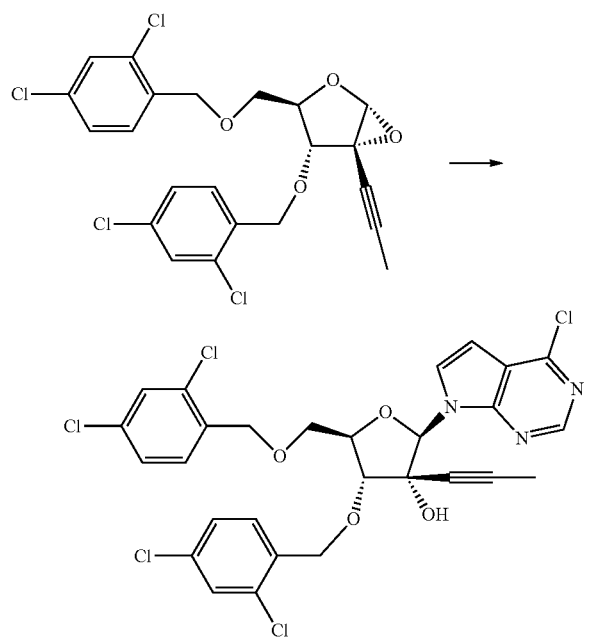

To a solution of 4-chloro-7H-pyrrolo[2,3-d]pyrimidine (0.374 g, 2.4 mol) in $CH_3CN$ (10 mL) was added NaH (60% suspension, 0.176 g, 4.0 mol) at 0° C. and the mixture was stirred at room temperature for 1 h. (1R,3R,4R,5R)-4-(2,4-dichlorobenzyloxy)-3-((2,4-dichlorobenzyloxy)methyl)-5-(prop-1-ynyl)-2,6-dioxabicyclo[3.1.0]hexane (1.20 g, 2.4 mol) in $CH_3CN$ (10 mL) was added to the reaction mixture. The resulting reaction mixture was heated to 50° C. for 16 h. After completion of the reaction, the mixture was concentrated under reduced pressure and poured into ice cold water. The mixture was extracted with EtOAc and the organic layer was washed with water and brine. The organic layer was dried over $Na_2SO_4$, filtered, and concentrated in vacuo. The residue was purified by silica gel column chromatography to give (2S,3R,4R,5R)-2-(4-chloro-7H-pyrrolo[2,3-d]pyrimidin-7-yl)-4-(2,4-dichlorobenzyloxy)-5-((2,4-dichlorobenzyloxy)methyl)-3-(prop-1-ynyl)tetrahydrofuran-3-ol (0.72 g, 1.12 mmol, yield 57% over two steps). $^1H$ NMR (DMSO-$d_6$, 400 MHz) δ 1.35 (s, 3H), 3.78 (dd, J=11.2, 3.6 Hz, 1H), 3.92 (dd, J=11.2, 2.4 Hz, 1H), 4.20 (dt, J=8.4, 3.6 Hz, 1H), 4.37 (d, J=8.4 Hz, 1H), 4.60 (ABq, J=12.8 Hz, 2H), 4.75 (d, J=13.2 Hz, 1H), 4.94 (d, J=12.8 Hz, 1H), 6.36 (s, 1H), 6.56 (s, 1H), 6.65 (d, J=4.0 Hz, 1H), 7.42-7.48 (m, 3H), 7.54 (d, J=8.0 Hz, 1H), 7.63 (dd, J=12.8, 1.6 Hz, 2H), 7.87 (d, J=3.2 Hz, 1H), 8.68 (s, 1H); LC-MS: m/z 640.05 $(M+H)^+$.

Synthesis of (2R,3R,4R,5R)-2-(4-amino-7H-pyrrolo[2,3-d]pyrimidin-7-yl)-4-((2,4-dichloro-benzyl)oxy)-5-(((2,4-dichlorobenzyl)oxy)methyl)-3-(prop-1-yn-1-yl)tetrahydrofuran-3-ol

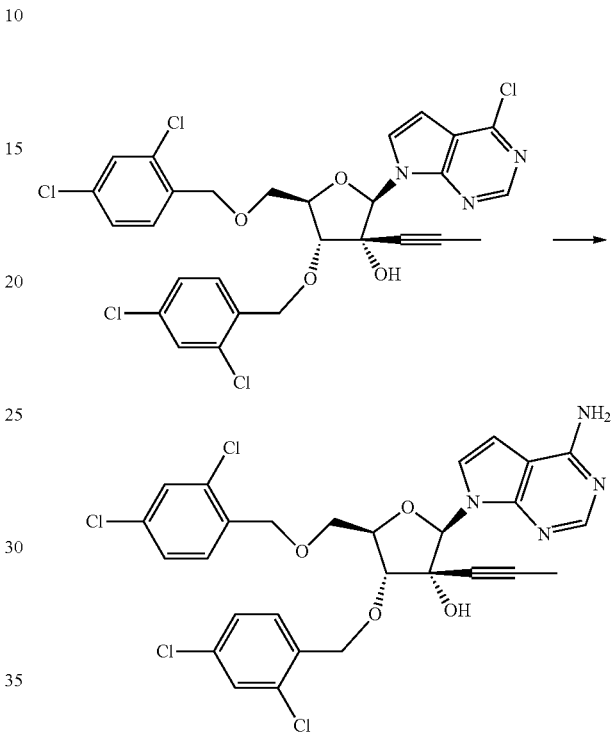

To a stirred solution of (2S,3R,4R,5R)-2-(4-chloro-7H-pyrrolo[2,3-d]pyrimidin-7-yl)-4-(2,4-dichlorobenzyloxy)-5-((2,4-dichlorobenzyloxy)methyl)-3-(prop-1-ynyl)tetrahydrofuran-3-ol (18.0 g, 0.028 mol) in liq. $NH_3$ (200 mL) in a steel bomb, the resultant reaction mixture was stirred at 60° C. for 48 h. After completion of the reaction, liq. $NH_3$ was removed under reduced pressure. The crude obtained was purified by column chromatography on neutral alumina, eluted with 5% gradient of MeOH in $CH_2Cl_2$ to afford (2S,3R,4R,5R)-2-(4-amino-7H-pyrrolo[2,3-d]pyrimidin-7-yl)-4-(2,4-dichlorobenzyloxy)-5-((2,4-dichlorobenzyloxy)methyl)-3-(prop-1-ynyl)tetrahydrofuran-3-ol (12.1 g, 0.019 mol, yield 69%). $^1H$ NMR (DMSO-$d_6$, 400 MHz) δ 1.40 (s, 3H), 3.75 (dd, J=11.2, 4.0 Hz, 1H), 3.87 (dd, J=13.2, 2.4 Hz, 1H), 4.11-4.13 (m, 1H), 4.35 (d, J=8.4 Hz, 1H), 4.57 (ABq, J=12.8 Hz, 2H), 4.77 (d, J=13.2 Hz, 1H), 4.96 (d, J=13.2 Hz, 1H), 6.25 (s, 1H), 6.36 (s, 1H), 6.50 (d, J=4.0 Hz, 1H), 6.96 (s, 2H), 7.27 (d, J=3.6 Hz, 1H), 7.39-7.47 (m, 3H), 7.56 (d, J=8.4 Hz, 1H), 7.61 (dd, J=5.6, 2.0 Hz, 2H), 8.06 (s, 1H); LC-MS: m/z 621.13 $(M+H)+$.

Synthesis of (2R,3R,4R,5R)-2-(4-amino-7H-pyrrolo[2,3-d]pyrimidin-7-yl)-5-(hydroxymethyl)-3-(prop-1-yn-1-yl)tetrahydrofuran-3,4-diol

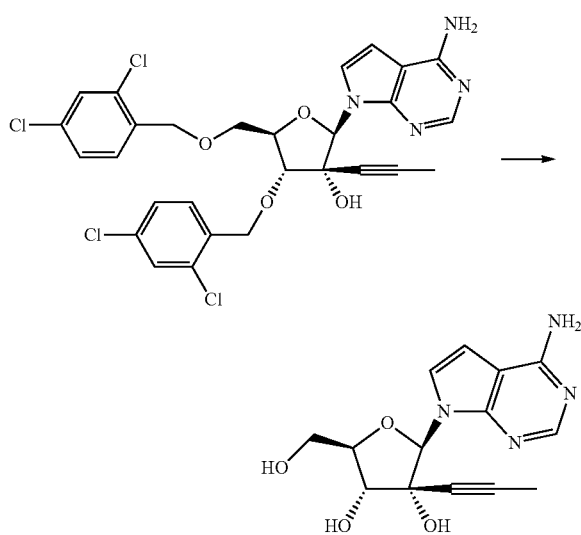

To a stirred solution of (2S,3R,4R,5R)-2-(4-amino-7H-pyrrolo[2,3-d]pyrimidin-7-yl)-4-(2,4-dichlorobenzyloxy)-5-((2,4-dichlorobenzyloxy)methyl)-3-(prop-1-ynyl)tetrahydrofuran-3-ol (12.0 g, 19 mmol) in $CH_2Cl_2$ (1200 mL) at −78° C. was added 1.0 M $BCl_3$ solution in $CH_2Cl_2$ (193 mL, 19 mmol). The reaction mixture was stirred at −78° C. for 2 h, followed by −20° C. for 6 h. After completion of the reaction, the reaction was quenched with MeOH (200 mL) in $CH_2Cl_2$ (300 mL) at −30° C. and the mixture was stirred for 30 min. The reaction mixture was neutralized with methanolic $NH_3$ at −20° C., and the resulting precipitates were filtered, and the filtrate was concentrated in vacuo. The residue was purified by silica gel column chromatography to give (3R,4R,5R)-2-(4-amino-7H-pyrrolo[2,3-d]pyrimidin-7-yl)-5-(hydroxymethyl)-3-(prop-1-ynyl)tetrahydrofuran-3,4-diol (4.0 g, 13.1 mmol, yield 60%). $^1$H NMR (DMSO-$d_6$, 400 MHz) δ 1.40 (s, 3H), 3.60-3.62 (m, 1H), 3.75-3.82 (m, 2H), 4.23 (t, J=7.6 Hz, 1H), 5.07 (br, 1H), 5.44 (d, J=7.2 Hz, 1H), 5.90 (s, 1H), 6.19 (s, 1H), 6.55 (d, J=3.6 Hz, 1H), 6.95 (s, 2H), 7.39 (d, J=4.0 Hz, 1H), 8.05 (s, 1H); LC-MS: m/z 305.28 (M+H)$^+$.

Synthesis of ((3aR,4R,6R,6aR)-6-(4-amino-7H-pyrrolo[2,3-d]pyrimidin-7-yl)-2,2-dimethyl-6a-(prop-1-yn-1-yl)tetrahydrofuro[3,4-d][1,3]dioxol-4-yl)methanol

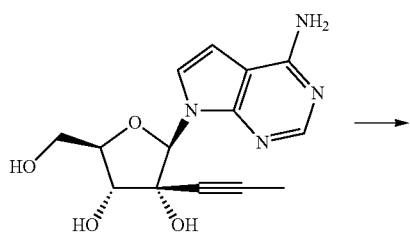

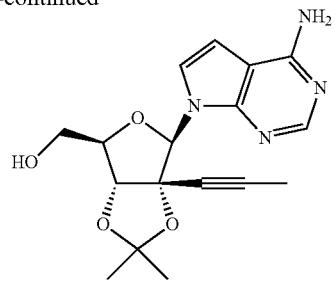

To a stirred solution of (3R,4R,5R)-2-(4-amino-7H-pyrrolo[2,3-d]pyrimidin-7-yl)-5-(hydroxymethyl)-3-(prop-1-ynyl)tetrahydrofuran-3,4-diol (0.95 g, 3.1 mmol) in acetone was added p-TsOH.H$_2$O (0.71 g, 3.7 mmol) followed by 2,2-dimethoxy propane (7.6 mL, 62.5 mmol) at room temperature. The resulting mixture was stirred at room temperature for 16 h. The reaction mixture was diluted with EtOAc and the organic layer was washed with sat. aq. NaHCO$_3$, water, and brine. The organic layer was dried over Na$_2$SO$_4$, filtered, and concentrated in vacuo. The residue was purified by silica gel column chromatography to give ((3aR,4R,6aR)-6-(4-amino-7H-pyrrolo[2,3-d]pyrimidin-7-yl)-2,2-dimethyl-6a-(prop-1-ynyl)tetrahydrofuro[3,4-d][1,3]dioxol-4-yl)methanol (0.79 g, 3.0 mmol, yield 73%). $^1$H NMR (DMSO-$d_6$, 400 MHz) δ 1.45 (s, 3H), 1.56 (s, 3H), 1.58 (s, 3H), 3.64-3.69 (m, 2H), 4.05 (dd, J=8.8, 4.4 Hz, 1H), 4.84 (d, J=4.4 Hz, 1H), 5.21 (t, J=6.0 Hz, 1H), 6.40 (s, 1H), 6.59 (d, J=3.2 Hz, 1H), 7.01 (s, 2H), 7.33 (d, J=3.2 Hz, 1H), 8.06 (s, 1H); LC-MS: m/z 345.29 (M+H)$^+$.

Synthesis of N-(7-((3aR,4R,6R,6aR)-6-(hydroxymethyl)-2,2-dimethyl-3a-(prop-1-yn-1-yl)tetrahydrofuro[3,4-d][1,3]dioxol-4-yl)-7H-pyrrolo[2,3-d]pyrimidin-4-yl)benzamide

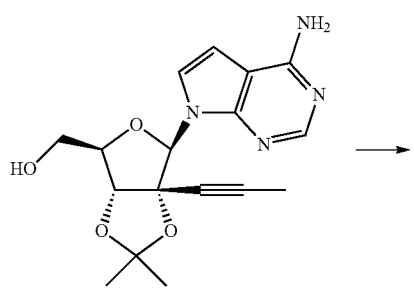

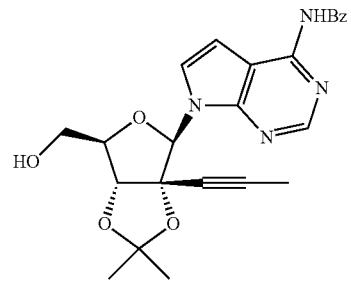

To a stirred solution of ((3aR,4R,6aR)-6-(4-amino-7H-pyrrolo[2,3-d]pyrimidin-7-yl)-2,2-dimethyl-6a-(prop-1-ynyl)tetrahydrofuro[3,4-d][1,3]dioxol-4-yl)methanol (0.20 g, 0.58 mmol) in pyridine (2.0 mL) was added TMSCl (0.23 mL, 1.8 mmol) at room temperature and the mixture was stirred at room temperature for 3 h. After the reaction mixture was cooled to 10° C., benzoyl chloride (0.08 mL, 0.69 mmol) was added and the mixture was stirred at room temperature for 16 h. The reaction mixture was diluted with EtOAc and the organic layer was washed with sat. aq. $KHSO_4$, water, and brine. The organic layer was dried over $Na_2SO_4$, filtered, and concentrated in vacuo. This crude material was treated with aq. ammonia solution and the mixture was stirred at room temperature for 4 h. The reaction mixture was diluted with EtOAc and organic layer was washed with water and brine. The organic layer was dried over $Na_2SO_4$, filtered, and concentrated in vacuo. The residue was purified by silica gel column chromatography to give N-(7-((3aR,6R,6aR)-6-(hydroxymethyl)-2,2-dimethyl-3a-(prop-1-ynyl)tetrahydrofuro[3,4-d][1,3]dioxol-4-yl)-7H-pyrrolo[2,3-d]pyrimidin-4-yl)benzamide (0.11 g, 0.25 mmol, yield 42%). $^1$H NMR (DMSO-$d_6$, 400 MHz) δ 1.46 (s, 3H), 1.57 (s, 3H), 1.59 (s, 3H), 3.68-3.73 (m, 2H), 4.13 (dd, J=9.6, 5.2 Hz, 1H), 4.89 (d, J=4.0 Hz, 1H), 5.21 (t, J=6.0 Hz, 1H), 6.59 (s, 1H), 6.70 (d, J=3.6 Hz, 1H), 7.55 (t, J=7.6 Hz, 2H), 7.65 (t, J=7.2 Hz, 1H), 7.69 (d, J=4.0 Hz, 1H), 8.08 (d, J=7.6 Hz, 2H), 8.63 (s, 1H), 11.13 (s, 1H); LC-MS: m/z 449.52 (M+H)$^+$.

Synthesis of N-(7-((2R,3R,4R,5 S)-3,4-dihydroxy-5-(((2-nitrophenyl)selanyl)methyl)-3-(prop-1-yn-1-yl)tetrahydrofuran-2-yl)-7H-pyrrolo[2,3-d]pyrimidin-4-yl)benzamide

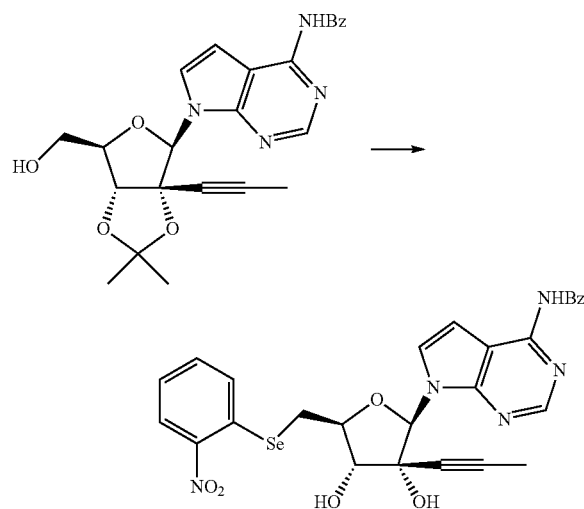

To a stirred solution of N-(7-((3aR,6R,6aR)-6-(hydroxymethyl)-2,2-dimethyl-3a-(prop-1-ynyl)tetrahydrofuro[3,4-d][1,3]dioxol-4-yl)-7H-pyrrolo[2,3-d]pyrimidin-4-yl)benzamide (1.60 g, 3.5 mmol) in THF (25 mL) was added 1-nitro-2-selenocyanatobenzene (1.62 g, 7.1 mmol) followed by n-Bu$_3$P (2.80 mL, 14 mol) at room temperature and the mixture was stirred at room temperature for 6 h. After completion of the reaction, reaction mixture was diluted with EtOAc and organic layer was washed with sat. aq. $NaHCO_3$ solution, water, and brine. The organic layer was dried over $Na_2SO_4$, filtered, and concentrated in vacuo. The obtained product was dissolved in trifluoroacetic acid (18 mL) and water (2 mL) and the mixture was stirred at room temperature for 4 h. After completion of the reaction, the solvent was evaporated under reduced pressure and the residue was purified by silica gel column chromatography to give N-(7-((3R,4R,5S)-3,4-dihydroxy-5-((2-nitrophenylselanyl)methyl)-3-(prop-1-ynyl)tetrahydrofuran-2-yl)-7H-pyrrolo[2,3-d]pyrimidin-4-yl)benzamide (2.0 g, 3.38 mmol, yield 95%). $^1$H NMR (DMSO-$d_6$, 400 MHz) δ 1.45 (s, 3H), 3.44-3.55 (m, 2H), 4.13-4.17 (m, 1H), 4.26-4.29 (m, 1H), 5.81 (d, J=6.8 Hz, 1H), 6.10 (s, 1H), 6.37 (s, 1H), 6.70 (d, J=3.6 Hz, 1H), 7.42 (t, J=7.2 Hz, 1H), 7.53-7.59 (m, 2H), 7.60-7.66 (m, 3H), 7.81 (d, J=8.4 Hz, 1H), 8.08 (d, J=7.6 Hz, 2H), 8.24 (d, J=8.0 Hz, 1H), 8.61 (s, 1H), 11.3 (s, 1H); LC-MS: m/z 594.45 (M+H)$^+$.

Synthesis of N-(7-((3R,4S)-3,4-dihydroxy-5-methylene-3-(prop-1-yn-1-yl)tetrahydrofuran-2-yl)-7H-pyrrolo[2,3-d]pyrimidin-4-yl)benzamide

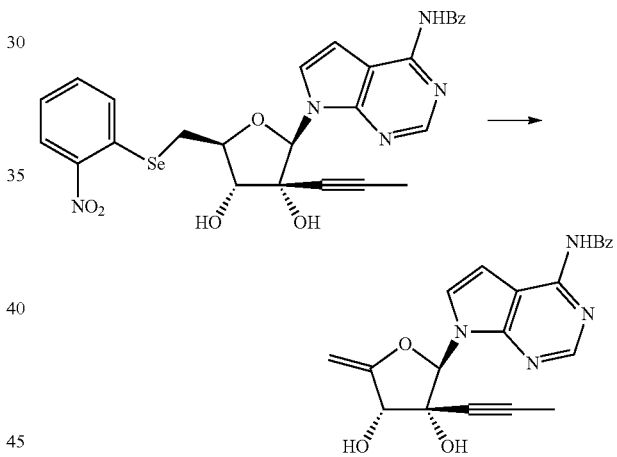

To a solution of N-(7-((3R,4R,5S)-3,4-dihydroxy-5-(((2-nitrophenyl)selanyl)methyl)-3-(prop-1-yn-1-yl)tetrahydrofuran-2-yl)-7H-pyrrolo[2,3-d]pyrimidin-4-yl)benzamide (1.31 g, 2.21 mmol) in THF (15 mL) was added 30% aq. $H_2O_2$ (1.4 mL, 13.9 mmol). The reaction mixture was stirred at room temperature for 1.5 h. To the reaction mixture were added Et$_3$N (1.9 mL, 13.9 mmol) and pyridine (5 mL). The reaction mixture was stirred at 50° C. for 35 h. After the bulk of solvent was concentrated, the residue was diluted with EtOAc. The mixture was washed with water and brine, dried over $Na_2SO_4$, filtered, and concentrated in vacuo. The residue was purified by silica gel column chromatography to give N-(7-((3R,4S)-3,4-dihydroxy-5-methylene-3-(prop-1-yn-1-yl)tetrahydrofuran-2-yl)-7H-pyrrolo[2,3-d]pyrimidin-4-yl)benzamide (340 mg, 0.871 mmol, yield 39%). $^1$H NMR (DMSO-$d_6$, 400 MHz) δ 1.75 (s, 3H), 4.25 (s, 1H), 4.42 (s, 1H), 4.92 (d, J=7.6 Hz, 1H), 5.91 (d, J=7.2 Hz, 1H), 6.31 (s, 1H), 6.59 (s, 1H), 6.74 (d, J=4.0 Hz, 1H), 7.54-7.57 (m, 3H), 7.65 (t, J=7.2 Hz, 1H), 8.08 (d, J=7.2 Hz, 2H), 8.65 (s, 1H), 11.16 (s, 1H); LC-MS: m/z 391.1 (M+H)$^+$.

Synthesis of N-(7-((3R,4S,5R)-5-fluoro-3,4-dihydroxy-5-(iodomethyl)-3-(prop-1-yn-1-yl)tetrahydrofuran-2-yl)-7H-pyrrolo[2,3-d]pyrimidin-4-yl)benzamide Synthesis of (2R,3S,4R)-5-(4-(N-benzoylbenzamido)-7H-pyrrolo[2,3-d]pyrimidin-7-yl)-2-fluoro-2-(iodomethyl)-4-(prop-1-yn-1-yl)tetrahydrofuran-3,4-diyl dibenzoate

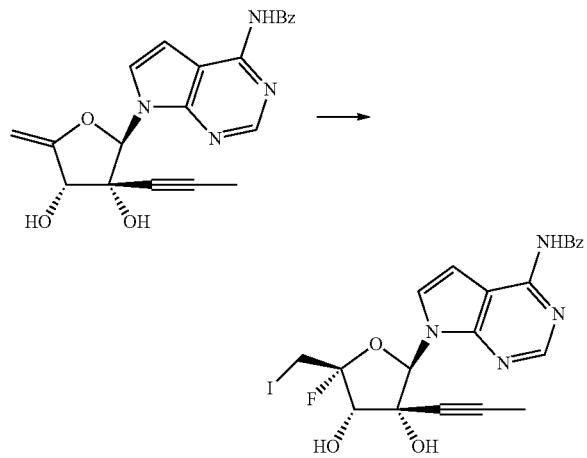

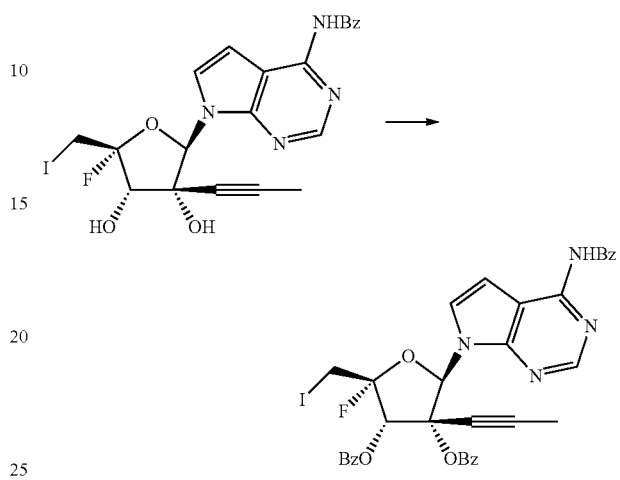

To a suspension of N-(7-((3R,4S)-3,4-dihydroxy-5-methylene-3-(prop-1-yn-1-yl)tetrahydrofuran-2-yl)-7H-pyrrolo[2,3-d]pyrimidin-4-yl)benzamide (359 mg, 0.92 mmol) in CH$_3$CN (4 mL) at 0° C. was added triethylamine trihydrofluoride (0.15 mL, 0.92 mmol) followed by a solution of N-iodosuccinimide (259 mg, 1.15 mmol) in CH$_3$CN (4 mL) slowly. The reaction mixture was stirred at 0° C. for 45 min and at room temperature for 40 min. Additional triethylamine trihydrofluoride (0.05 mL, 0.31 mmol) and a solution of N-iodosuccinimide (100 mg, 0.39 mmol) in CH$_3$CN (1 mL) were added at 0° C., and the mixture was stirred at 0° C. for 20 min and at room temperature for 30 min. The reaction mixture was poured into a solution of aq. NaHCO$_3$ and Na$_2$S$_2$O$_3$. The resulting precipitate was collected by filtration and washed with EtOAc and water, and dried to obtain the desired product. The filtrate was extracted with EtOAc. The organic extract was washed with water and brine, dried over Na$_2$SO$_4$, filtered, and concentrated in vacuo. The residue was triturated with EtOAc-cyclohexane and the solid was collected by filtration to give the additional product. The filtrate was concentrated and the residue was purified by silica gel column chromatography to the additional product. The obtained products were combined to give N-(7-((3R,4S,5R)-5-fluoro-3,4-dihydroxy-5-(iodomethyl)-3-(prop-1-yn-1-yl)tetrahydrofuran-2-yl)-7H-pyrrolo[2,3-d]pyrimidin-4-yl)benzamide (434 mg, 0.809 mmol, yield 88%). $^1$H NMR (DMSO-d$_6$, 400 MHz) δ 1.43 (s, 3H), 3.63 (dd, J=11.6, 4.0 Hz, 1H), 3.79 (dd, J=26.8, 11.6 Hz, 1H), 4.72 (dd, J=18.4, 9.2 Hz, 1H), 6.01 (d, J=8.8 Hz, 1H), 6.25 (s, 1H), 6.61 (s, 1H), 6.73 (d, J=4.0 Hz, 1H), 7.55 (t, J=7.2 Hz, 1H), 7.62-7.67 (m, 2H), 8.07 (d, J=7.2 Hz, 2H), 8.65 (s, 1H), 11.16 (s, 1H); LC-MS: m/z 537.1 (M+H)$^+$.

To a solution of N-(7-((3R,4S,5R)-5-fluoro-3,4-dihydroxy-5-(iodomethyl)-3-(prop-1-yn-1-yl)tetrahydrofuran-2-yl)-7H-pyrrolo[2,3-d]pyrimidin-4-yl)benzamide (434 mg, 0.809 mmol) in pyridine (4 mL) at 0° C. was added benzoyl chloride (0.94 mL, 8.09 mmol). The reaction mixture was stirred at 0° C. for 5 min and at room temperature for 10 h. After dilution with EtOAc, the mixture was washed with aq. KHSO$_4$ (×2), aq. sat. NaHCO$_3$ (×2), water, and brine, dried over Na$_2$SO$_4$, filtered, and concentrated in vacuo. The residue was purified by silica gel column chromatography to give (2R,3S,4R)-5-(4-(N-benzoylbenzamido)-7H-pyrrolo[2,3-d]pyrimidin-7-yl)-2-fluoro-2-(iodomethyl)-4-(prop-1-yn-1-yl)tetrahydrofuran-3,4-diyl dibenzoate (725 mg, 0.854 mmol, yield 100%). $^1$H NMR (DMSO-d$_6$, 400 MHz) δ 1.38 (s, 3H), 3.89-3.94 (m, 2H), 6.62 (d, J=4.0 Hz, 1H), 6.77 (d, J=16.0 Hz, 1H), 7.22 (s, 1H), 7.46-7.64 (m, 9H), 7.70-7.75 (m, 2H), 7.82-7.86 (m, 4H), 7.92-7.95 (m, 2H), 8.00-8.04 (t, J=7.6 Hz, 4H), 8.69 (s, 1H); LC-MS: m/z 849.5 (M+H)$^+$.

Synthesis of (2S,3S,4R,5R)-5-(4-benzamido-7H-pyrrolo[2,3-d]pyrimidin-7-yl)-2-((benzoyloxy)methyl)-2-fluoro-4-(prop-1-yn-1-yl)tetrahydrofuran-3,4-diyl dibenzoate

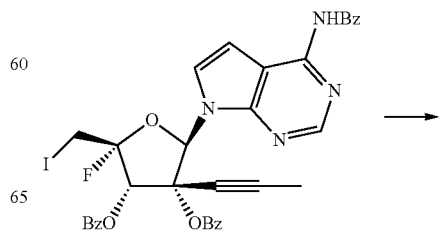

-continued

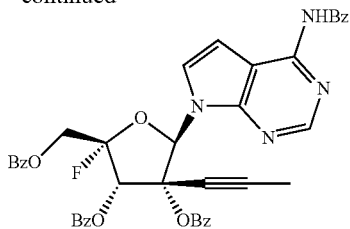

To a solution of (2R,3S,4R,5R)-5-(4-(N-benzoylbenzamido)-7H-pyrrolo[2,3-d]pyrimidin-7-yl)-2-fluoro-2-(iodomethyl)-4-(prop-1-yn-1-yl)tetrahydrofuran-3,4-diyl dibenzoate (725 mg, 0.854 mmol) in DMSO (8 mL) were added sodium benzoate (1.23 g, 8.54 mmol) and 15-crown-5 (1.7 mL, 8.54 mmol). The reaction mixture was stirred at 100° C. for 22 h. Additional sodium benzoate (0.6 g, 4.16 mmol) and 15-crown-5 (0.7 mL, 3.53 mmol) were added. After being stirred at 100° C. for 22 h, additional sodium benzoate (0.6 g, 4.16 mmol) and 15-crown-5 (0.7 mL, 3.53 mmol) were added. After being stirred at 100° C. for 7 h, the mixture was diluted with EtOAc, filtered through the pad of celite. The filtrate was washed with sat. aq. NaHCO$_3$ (×2) and water, and dried over Na$_2$SO$_4$, filtered, and concentrated in vacuo. The residue was purified by silica gel column chromatography to give (2S,3S,4R)-5-(4-benzamido-7H-pyrrolo[2,3-d]pyrimidin-7-yl)-2-((benzoyloxy)methyl)-2-fluoro-4-(prop-1-yn-1-yl)tetrahydrofuran-3,4-diyl dibenzoate (541 mg, 0.498 mmol, yield 58%). $^1$H NMR (DMSO-d$_6$, 400 MHz) δ 1.46 (s, 3H), 4.90 (t, J=11.6 Hz, 1H), 5.02 (dd, J=18.0, 12.0 Hz, 1H), 5.75 (s, 1H), 6.79 (d, J=3.2 Hz, 1H), 6.97 (d, J=15.2 Hz, 1H), 7.32-7.37 (m, 3H), 7.52-7.78 (m, 10H), 7.89 (d, J=7.6 Hz, 2H), 8.00 (d, J=8.0 Hz, 2H), 8.05 (d, J=7.2 Hz, 2H), 8.10 (d, J=7.2 Hz, 2H), 8.68 (s, 1H), 11.25 (s, 1H); LC-MS: m/z 739.4 (M+H)$^+$.

Synthesis of (2S,3S,4R,5R)-5-(4-amino-7H-pyrrolo [2,3-d]pyrimidin-7-yl)-2-fluoro-2-(hydroxymethyl)-4-(prop-1-yn-1-yl)tetrahydrofuran-3,4-diol (Example 1)

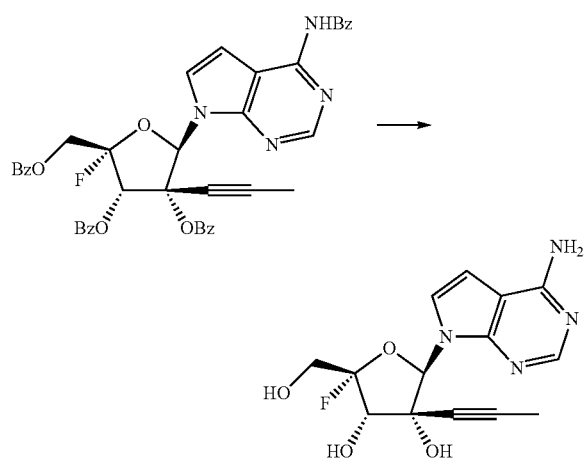

(2S,3 S,4R,5R)-5-(4-benzamido-7H-pyrrolo[2,3-d]pyrimidin-7-yl)-2-((benzoyloxy)methyl)-2-fluoro-4-(prop-1-yn-1-yl)tetrahydrofuran-3,4-diyl dibenzoate (541 mg, 0.732 mmol) was dissolved in 33% methylamine solution in ethanol. After the resulting mixture was stirred at room temperature for 16 h, the bulk of solvent was concentrated in vacuo. The residue was purified by silica gel column chromatography to give (2S,3S,4R)-5-(4-amino-7H-pyrrolo[2,3-d]pyrimidin-7-yl)-2-fluoro-2-(hydroxymethyl)-4-(prop-1-yn-1-yl)tetrahydrofuran-3,4-diol (183 mg, 0.568 mmol, yield 78%). $^1$H NMR (DMSO-d$_6$, 400 MHz) δ 1.39 (s, 3H), 3.56-3.62 (m, 2H), 4.51 (dd, J=19.3, 6.8 Hz, 1H), 5.62 (t, J=5.6 Hz, 1H), 5.69 (d, J=7.9 Hz, 1H), 6.10 (s, 1H), 6.52 (s, 1H), 6.60 (d, J=3.6 Hz, 1H), 7.02 (s, 2H), 7.26 (d, J=3.8 Hz, 1H), 8.09 (s, 1H); $^{19}$F NMR (DMSO-d$_6$, 376 MHz) δ −119.96; LC-MS: m/z 323.3 (M+H)$^+$.

Example 2

Synthesis of ((2S,3S,4R,5R)-5-(4-amino-7H-pyrrolo [2,3-d]pyrimidin-7-yl)-2-fluoro-3,4-dihydroxy-4-(prop-1-yn-1-yl)tetrahydrofuran-2-yl)methyl bis(((1-isopropoxycarbonyl)oxy) methyl) phosphate (Example 2)

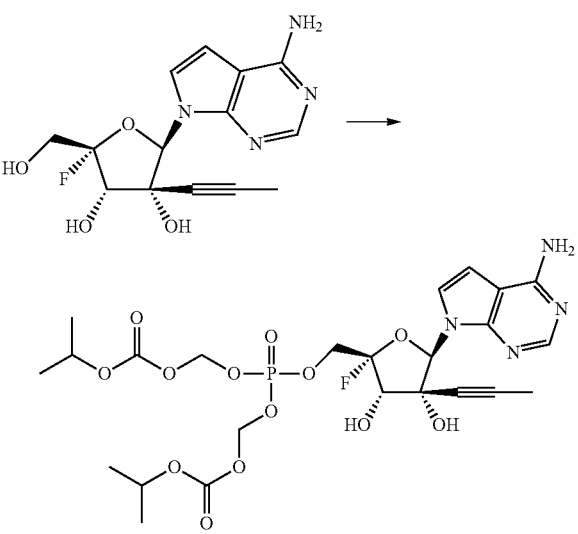

In a scintillation vial, the starting phosphonic acid (200 mg, 0.61 mmol, ((hydroxyphosphoryl)bis(oxy))bis(methylene) diisopropyl dicarbonate) and the nucleoside of Example 1 (64 mg, 0.20 mmol, (2S,3S,4R,5R)-5-(4-amino-7H-pyrrolo[2,3-d]pyrimidin-7-yl)-2-fluoro-2-(hydroxymethyl)-4-(prop-1-yn-1-yl)tetrahydrofuran-3,4-diol) were suspended in pyridine (2 mL). 1-Methyl imidazole (247 mg, 3.0 mmol) was added and the mixture was sonicated for 30 seconds. The mixture was then evaporated to a residue by rotary evaporation for 20 minutes. The residue was then resuspended in CH$_3$CN (2 mL) and sonicated for 30 seconds. The reaction was fitted with a stir bar and stirring was commenced. BOP-Cl (280 mg, 1.1 mmol, bis(2-oxooxazolidin-3-yl)phosphinic chloride) was then added as a solid and the reaction was stirred at room temperature for 3 h. The reaction was monitored by LC/MS. When the reaction was deemed complete, water (1 mL) was added to quench. The reaction was stirred for 10 minutes and then frozen and lyophilized to dryness. The residue was purified by prep-HPLC to give the desired product (60 mg, 0.076 mmol, y 38%). $^1$H NMR (CD$_3$OD, 400 MHz) δ 1.28 (d, J=12 Hz, 12H), 1.47 (s, 3H), 4.34-4.42 (m, 2H), 4.66 (d, J=16 Hz, 1H), 4.86-4.93 (m, 2H), 5.62-5.69 (m, 4H), 6.63 (s, 1H), 6.95 (d, J=4 Hz, 1H), 7.47 (d, J=4 Hz, 1H), 8.31 (s, 1H); $^{31}$P NMR (CD$_3$OD, 162 MHz) δ -5.22; LC-MS: m/z 635.2 (M+H)$^+$.

Example 3

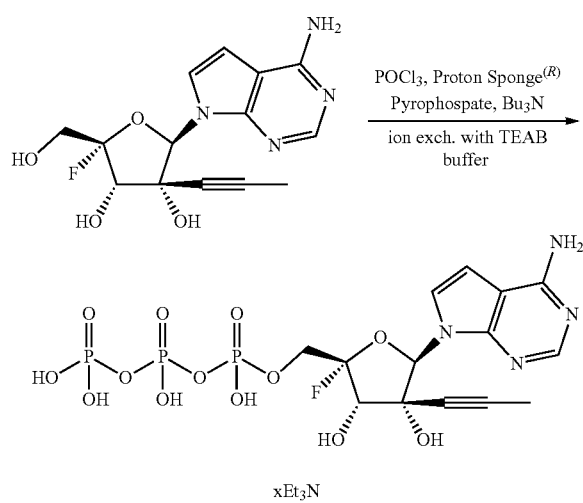

To the compound of Example 1 (9 mg, 0.028 mmol), in P(=O)(OMe)$_3$ (0.3 mL) at r.t. was added POCl$_3$ (0.031 mL, 0.335 mmol) and the mixture was stirred for 2 min. Proton Sponge® (1,8-bis(dimethylamino)naphthalene: 20.95 mg, 0.098 mmol) was added and the reaction was stirred at r.t for 30 min (first batch) or 2 hr (second batch), then quenched by adding a mixture of Pyrophosphate (250 mg, 0.456 mmol) in 1 ml of DMF and Bu$_3$N (0.106 mL, 0.447 mmol). The reaction was stirred for 15 min. After the completion of triphosphate conversion, the crude reaction mixture was added to 0.2N triethylammonium bicarbonate (TEAB) buffer (20 ml) and stirred for 10 min, then lyophilized to a semi-solid and purified as described below. The reaction was repeated with the same scale, and the two batches were combined for purification.

Purification:

The combined crude triphosphate was purified by PREP ion exchange chromatography using a triphosphate purification gradient (PREP ion exchange chromatography, flow at 8 ml/min): starting from 100% water, gradient from 0% to 80% TEA bicarbonate buffer (0.5 N)/water in 30 min, followed by 80% TEA bicarbonate buffer (0.5 N)/water for 5 min, then 100% water for 5 min. The desired triphosphate was eluted at 27 min as a broad peak (3 injections). The desired product fractions were lyophilized, then dissolved in water for a second purification by C18 column (PREP C18 reverse phase Chromatography, Flow at 20 ml/min) using a gradient starting from 100% TEA bicarbonate buffer (0.2 N), followed by a gradient of Acetonitrile/TEA bicarbonate buffer (0.2 N) from 0% to 30% in 20 min. The desired product eluted at around 11 min. As the product obtained from the second C18 purification contained what appeared to be diphosphate and over-phosphorylated impurities, it was purified again by a third PREP ion exchange chromatography, followed by a fourth purification by C18 column as mentioned above to give 001 (Example 3: 8.7 mg, 9.85 μmol, 15.79% yield).

$^1$H NMR (400 MHz, Deuterium Oxide)$^1$H NMR (400 MHz, Deuterium Oxide) δ 8.14 (s, 1H), 7.42 (d, J=3.8 Hz, 1H), 6.68 (d, J=3.8 Hz, 1H), 6.60 (s, 1H), 4.75 (d, J=1.4 Hz, 1H), 4.30 (ddd, J=11.4, 6.2, 2.7 Hz, 1H), 4.24-4.14 (m, 1H), 3.13 (q, J=7.3 Hz, 18H), 1.29 (s, 3H), 1.21 (t, J=7.3 Hz, 29H). 31P: -9.42, -9.55, -12.07, -12.19, -22.78, -22.90, -23.02

Based on $^1$H NMR, the ratio of Nucleoside Triphosphate to Et$_3$N in the salt is 1/3.0 The Formula weight is 865.801.

Biological Assays and Data

The activity of a compound according to the present invention can be assessed by methods known in the art; the following methods were used to produce the data in the following Tables.

HRV Cytopathic Effect (CPE) Assay.

Compounds were serially diluted in DMSO in half-logarithmic steps starting from 5 mM. Of each dilution, 0.5 μL were transferred to the assay plates. H1-HeLa cells were added to the assay-ready compound plates in 45 μL DMEM supplemented with 0.1% BSA (Gibco, 15260), 1× penicillin/streptomycin solution (CellGro/Mediatech, Manassas, Va.; 30-002-CI), and 1× non-essential amino acids (CellGro; 25-025-CI) at 5000 cells/well into triplicate 384-well plates and incubated at 33° C. for 6 hours. Control wells included DMSO alone (100% inhibition) and DMSO plus virus (0% inhibition). After 6 h incubation at 33° C., 5 μL of human rhinovirus stock was added at an MOI that effectively kills 99% of cells within 72 hours. Plates were then incubated for 72 h at 33° C. Cell viability was determined using the CellTiter-Glo® Luminescent Cell Viability Assay (Promega, G7573) according to the manufacturer's protocol and a POLARstar Omega Luminometer (BMG Labtech).

HRV Replicon Assay.

This assay was based on the Group C replicon previously described (Mello et al, *Antimicrobial Agents and Chemotherapy*, 2014) with the modification that the P1 region was replaced with the cDNA encoding Nanoluciferase (Promega Corporation, Madiso, Wis.) Compounds were serially diluted in DMSO in half-logarithmic steps starting from 5 mM. Of each dilution, 0.5 μL were transferred to the assay plates. H1-HeLa cells were trypsinized, washed twice with ice-cold OptiMem® Gibco, 31985), resuspended at 1.5×10$^7$ cells/ml in OptiMem®, and stored on ice. A total of 6×10$^6$ cells were electroporated (270 V, 950 μF, ∞ resistance) with 25 ng of in vitro-transcribed RNA and allowed to rest on ice for 10 min. Electroporated cells were then diluted DMEM supplemented with 0.1% BSA (Gibco, 15260), 1× penicillin/streptomycin solution (CellGro/Mediatech, Manassas, Va.; 30-002-CI) to a final concentration 4×10$^5$ cells/ml. 50 μl of cells were then added to the compounds then incubated for 72 h at 33° C. Luciferase signal was then measured after 48 h using the NanoGlo® Detection Kit Assay (Promega, N1150) according to the manufacturer's protocol and a POLARstar Omega Luminometer (BMG Labtech).

MT4 and PC3 Cytotoxicity Assay.

Compounds were serially diluted in DMSO in half-logarithmic steps starting from 10 mM. 0.5 μL of serially diluted compound was transferred to the assay plates (Greiner cat#781080). Cells were added to the assay-ready compound plates in 50 μL of RPMI 1640 medium supplemented with 10% FBS (NCS Lot OS-161071), 1× penicillin/streptomycin solution (CellGro/Mediatech, Manassas, Va.; 30-002-CI), and incubated at 37° C. for 3 or 5 days. Control wells included DMSO alone (100% inhibition). Cell viability was determined using the CellTiter-Glo® Luminescent Cell Viability Assay (Promega, G7573) according to the manufacturer's protocol and a POLARstar Omega Luminometer (BMG Labtech).

Human DNA Polymerase Gamma Assay.

Human DNA polymerase gamma single nucleotide Incorporation assay was adapted from Clark et al. (Discovery of beta-D-20-deoxy-20-a-fluoro-40-a-cyano-5-aza-7,9-dideaza adenosine as a potent nucleoside inhibitor of respiratory syncytial virus with excellent selectivity over mitochondrial RNA and DNA polymerases. BMCL, 25: 2484-2487.). Briefly, 200 nM of recombinant human DNA polymerase gamma (large subunit; POLG) and 400 nM recombinant human DNA polymerase accessory subunit (POLG2) were pre-incubated on ice for 2 min. Elongation complexes with RNA were formed by addition of 150 nM annealed DNA primer/DNA template duplex, in assay buffer (50 mM Tris/HCl, pH 8, 10 mM $MgCl_2$, 50 mM NaCl, 1 mM DTT) for 1.5 min at room temperature (RT), followed by rapid mixing with 100 μM nucleoside triphosphate substrate or inhibitor. Recombinant POLG (aa 30-1239) and POLG2 (aa 26-485) proteins were purified from E. coli and stored in 5 mM Tris pH7.5, 250 mM NaCl, 10% glycerol, 0.005% NP40 and POLG2 (aa 26-485) and 50 mM Tris pH7.5, 150 mM NaCl, 1 mM TCEP, 0.005% NP40, 10% glycerol, respectively. The volume of POLRMT added to any reaction was always less than or equal to one-tenth the total volume. Primer-template consisted of a 5'-FAM labeled 18-mer DNA oligonucleotide primer (5'-TTTTGTCTTTGTACTAGGAGGC-3') annealed to the appropriate 34-mer DNA template to allow single addition of A, C, G or U deoxy- or ribonucleotide (Clark et al. 2012). Reactions were allowed to proceed for 1 min at RT and quenched by addition of EDTA (50 mM). Products were resolved from substrates by denaturing PAGE. An equal volume of loading buffer (95% formamide, 18 mM EDTA, and 0.025% SDS, xylene cyanol, and bromophenol blue; Ambion, USA) was added to the quenched reaction mixtures and heated to 65° C. for 5 min prior to loading on a denaturing 20% polyacrylamide gel containing 1×TBE (89 mM Tris base, 89 mM boric acid, 2 mM EDTA) and 7 M Urea. Electrophoresis was performed in 1×TBE buffer at 600 V. Gels were visualized with a Typhoon Imager under fluorescence detection mode and quantified with the Image Quant™ TL Software (GE Healthcare, Piscataway, N.J.). DNA oligonucleotides were ordered from Sigma Aldrich, USA.

Human Mitochondrial RNA Polymerase Assay.

Human mitochondrial RNA polymerase (POLRMT) single nucleotide Incorporation assay was adapted from Arnold et al. (Sensitivity of mitochondrial transcription and resistance of RNA polymerase II dependent nuclear transcription to antiviral ribonucleosides. PloS Pathogen 8(11): e1003030.). Briefly, elongation complexes were formed by incubating 500 nM POLRMT with 250 nM annealed DNA template/RNA primer duplex, in assay buffer (25 mM Tris-HCl, pH 8, 50 mM KCl, 10 mM $MgCl_2$, 1 mM dithiothreitol, 0.2 U/μL RNasin) for 1.5 min at room temperature (RT), followed by rapid mixing with 500 μM nucleoside triphosphate substrate or inhibitor. Purified full length POLRMT (Enzymax, USA) was stored in 10 mM Tris-HCl (pH 8.0), 1 mM DTT, 100 mM NaCl and 20% glycerol. The volume of POLRMT added to any reaction was always less than or equal to one-tenth the total volume. Primer-template consisted of a 5'-FAM labeled 8-mer RNA oligonucleotide primer (5'-UUUUGCCGCGCC-3') annealed to the appropriate 18-mer DNA template to allow single addition of A, C, G or U ribonucleotide (Arnold et al. 2012). Reactions were allowed to proceed for 5 min at RT and quenched by addition of EDTA (50 mM). Products were resolved from substrates by denaturing PAGE. An equal volume of loading buffer (95% formamide, 18 mM EDTA, and 0.025% SDS, xylene cyanol, and bromophenol blue; Ambion, USA) was added to the quenched reaction mixtures and heated to 65° C. for 5 min prior to loading on a denaturing 23% polyacrylamide gel containing 1×TBE (89 mM Tris base, 89 mM boric acid, 2 mM EDTA) and 7 M urea. Electrophoresis was performed in 1×TBE buffer at 600 V. Gels were visualized with a Typhoon Imager under fluorescence detection mode and quantified with the Image Quant TL Software (GE Healthcare, Piscataway, N.J.). DNA and RNA oligonucleotides were ordered from Sigma Aldrich, USA.

DENV Polymerase De Novo Initiation and Elongation Assays for HTS:

1) De Novo Fluorescence-Based Alkaline Phosphatase-Coupled Polymerase Assay (De Novo FAPA):

Briefly, the assay was carried out sequentially in 20 μL final volume as follows: 0.25 uL compound dissolved in 90% DMSO and 10% water was stamped into 384-well high-base medium-binding black plates, control wells received DMSO/water mixture only. 5 μL of a 200 nM DENV4 RdRp protein stock solution in enzyme assay buffer was dispensed to assay plates and pre-incubated for 15 minutes at 25° C. in a humidity controlled incubator. To initiate the enzyme reaction, 5 μL of 200 nM DENV4 IVT RNA substrate and 40 μM GTP, ATP, UTP and 10 μM Atto-CTP substrate was added to all wells, at which point the plates were incubated in a humidity controlled incubator at 25° C. for 2 hour. RNA and NTP substrate mixtures were similarly prepared in enzyme assay buffer. Final reaction conditions contained 100 nM enzyme, 100 nM RNA, 20 μM NTPs and 5 μM ATTO-CTP. Neutral controls (high activity controls) consisted of 100 nM enzyme, 100 nM RNA, 20 μM NTP and 5 μM ATTO-CTP. Activity controls (low activity baseline controls) consisted of 1× assay buffer, 100 nM RNA, 20 μM NTP and 5 μM ATTO-CTP. To terminate the reactions, 10 μL stop solution containing 20 nM CIP (calf intestinal phosphatase) was dispensed to all wells and plates were incubated for 1 hour at 25° C. The stop solution to dilute CIP was prepared in AttoPhos® buffer (2.4 M DEA pH 10, 0.057 mM $MgCl_2$ and 0.85 mM $NaN_3$) with additional 20 mM $MgCl_2$ and 160 mM NaCl, and stored at 4° C. A Tecan Infinite® M6 reader was used for the fluorescent signal readout, using an excitation wavelength at 420 nm and emission wavelength at 560 nm, and a gain of 255 Flashes: 50.

Cytotoxicity (CC50 Assay) in HepG2 & K562

White TC grade Greiner 384-well assay plates were stamped with 0.5 ul of compound in 90% DMSO/10% water. HepG2 cells were trypsinized and collected into 50 ml falcon tube. K562 suspension cells were collected in 50 ml falcon tube. Both tubes containing cells were spun in benchtop centrifuge at 1200 rpm for 5 mins. The supernatant was discarded and the cell pellet was re-suspended in fresh culture media (HepG2: DMEM:F12 mix+10% FBS+1% Pen/Strep & K562: IMDM+10% FBS+1% Pen-Strep). Cells were counted using a hemocytometer and cells were diluted to a working suspension of 50,000 cells/ml for HepG2, and 20,000 cells/ml for K562. 50 ul of cells suspension was added to each well of 384-assay plate. Assay plates were incubated at 37° C., 5% $CO_2$, 90% humidity incubator for 72 hours. Assay plates were then treated with 25 ul of Promega's Cell-Titer Glo® reagent, and incubated at room temperature for 10 mins. Plates were read on PolarStar-Omega using the Luminescence setting and a Gain of 3300.

Using the assays described above, compounds of the invention exhibit antiviral efficacy as summarized in the following tables. This 4'-azido-cytidine was used as a control:

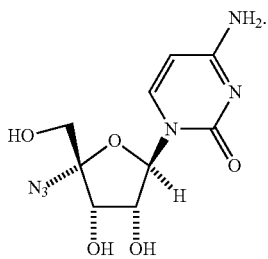 [SMILES: [N-]=[N+]=N[C@]1(CO)O[C@@H](n2ccc(N)nc2=O)[C@H](O)[C@@H]1O]

Activity and Cytotoxicity of the Compound of EXAMPLE 2.

| Activity on HRV strains and other viruses | μM |
|---|---|
| HRV16 | 0.6 |
| HRV14 | 0.7 |
| HRV29 | 0.7 |
| HRV10 | 0.8 |
| HRV86 | 0.4 |
| HRV39 | 0.6 |

| Activity on HRV strains and other viruses | μM |
|---|---|
| HRV15 (c-type) | 0.7 |
| Chikungunya virus | 1.0 |
| Dengue virus (PBMCs) | 2.05 |

| Cytotoxicity Assay Results | μM |
|---|---|
| MT4 (N = 2) | >100 |
| K562 ((N = 3) | >100 |
| HepG2 (N = 7$_+$) | >100 |
| PC3 | >200 |

Activity of Derivatives of Example 1.

| Polymerase assay (TP) | |
|---|---|
| HRV 3D Polymerase (5'-monophosphate of the compound of EXAMPLE 1) | IC50 = 3.4 uM |
| Dengue NS5 Polymerase (5'-monophosphate of the compound of EXAMPLE 1) | IC50 = 8.3 uM |
| Human Mitochondrial RNA polymerase incorporation | 1.9% (Example 3) 1.9% (Sofosbuvir TP) |
| Human Mitochondrial DNA polymerase γ incorporation (5'-monophosphate of the compound of EXAMPLE 1) | 0% |
| Cellular assays (MP-Nuc) | |
| PC-3 Cox/SDH ratio <0.5 (Example 2) | >200 uM |
| 4'-Azido cytidine (control) | 25 uM |
| HepG2 Cox/SDH ratio <0.5 (Example 2) | >200 uM |
| 4'-Azido cytidine (control) | 200 uM |

The foregoing data demonstrates that the nucleosides of Formula (I) provide potent activity against a variety of HRV serotypes as well as other viruses, while exhibiting low potential for toxicity on mammalian cells as measured by commonly used cytotoxicity models (MT4, PC-3, etc.), low potential for mitochondrial toxicity as measured by human mitochondrial polymerase incorporation assays (DNA Polymerase γ and RNA polymerase), and low cell culture mitochondrial toxicity based on the Cox/SDH ratio assay.

The invention claimed is:
1. The compound:

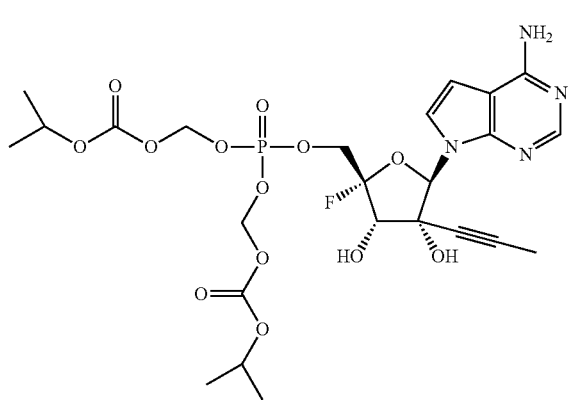 [SMILES: CC#C[C@]1(O)[C@H](n2ccc3c(N)ncnc32)O[C@](F)(COP(=O)(OCOC(=O)OC(C)C)OCOC(=O)OC(C)C)[C@H]1O]

or a pharmaceutically acceptable salt thereof.

2. A pharmaceutical composition comprising a compound of claim 1 or a pharmaceutically acceptable salt thereof and one or more pharmaceutically acceptable carriers.

3. A combination comprising a therapeutically effective amount of a compound according to claim 1 or a pharmaceutically acceptable salt thereof and one or more therapeutically active co-agents.

4. A method of treating an HRV infection or a chikungunya infection, comprising administering to a subject in need thereof a therapeutically effective amount of a compound of claim 1 or a pharmaceutically acceptable salt thereof.

5. The compound:

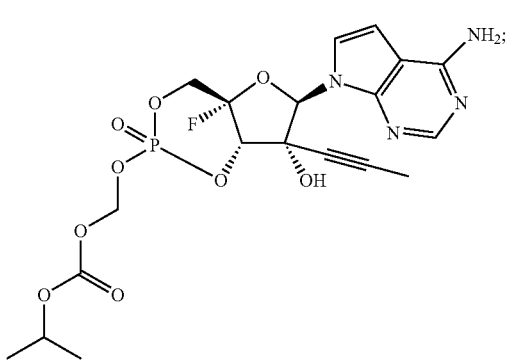

or a pharmaceutically acceptable salt thereof.

6. A pharmaceutical composition comprising a compound of claim 5 or a pharmaceutically acceptable salt thereof and one or more pharmaceutically acceptable carriers.

7. A combination comprising a therapeutically effective amount of a compound according to claim 5 or a pharmaceutically acceptable salt thereof and one or more therapeutically active co-agents.

8. A method of treating an HRV infection or a chikungunya infection, comprising administering to a subject in need thereof a therapeutically effective amount of a compound of claim 5 or a pharmaceutically acceptable salt thereof.

9. The compound:

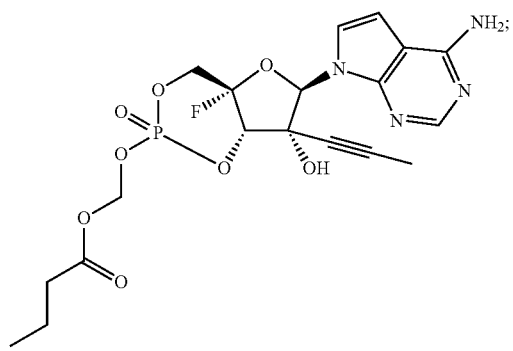

or a pharmaceutically acceptable salt thereof.

10. A pharmaceutical composition comprising a compound of claim 9 or a pharmaceutically acceptable salt thereof and one or more pharmaceutically acceptable carriers.

11. A combination comprising a therapeutically effective amount of a compound according to claim 9 or a pharmaceutically acceptable salt thereof and one or more therapeutically active co-agents.

12. A method of treating an HRV infection or a chikungunya infection, comprising administering to a subject in need thereof a therapeutically effective amount of a compound of claim 9 or a pharmaceutically acceptable salt thereof.

13. The compound:

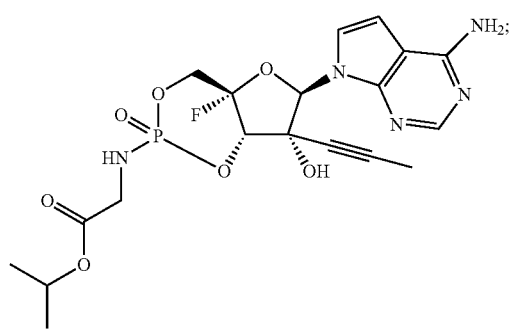

or a pharmaceutically acceptable salt thereof.

14. A pharmaceutical composition comprising a compound of claim 13 or a pharmaceutically acceptable salt thereof and one or more pharmaceutically acceptable carriers.

15. A combination comprising a therapeutically effective amount of a compound according to claim 13 or a pharmaceutically acceptable salt thereof and one or more therapeutically active co-agents.

16. A method of treating an HRV infection or a chikungunya infection, comprising administering to a subject in need thereof a therapeutically effective amount of a compound of claim 13 or a pharmaceutically acceptable salt thereof.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
ttttgtcttt gtactaggag gc                                            22

<210> SEQ ID NO 2
<211> LENGTH: 12
<212> TYPE: RNA
<213> ORGANISM: Homo sapiens

<400> SEQUENCE: 2
uuuugccgcg cc                                                       12